US011511456B2

(12) United States Patent
Rashid et al.

(10) Patent No.: US 11,511,456 B2
(45) Date of Patent: Nov. 29, 2022

(54) BINDER MATERIALS

(71) Applicant: Materialize.X Limited, London (GB)

(72) Inventors: Haidin Farmin Rashid, Birmingham (GB); Fabio Fiorelli, London (GB); Adrien Stephane Hitz, London (GB); Michael Brand, Baden (CH)

(73) Assignee: Materialize.X Limited, London (GB)

( * ) Notice: Subject to any disclaimer, the term of this patent is extended or adjusted under 35 U.S.C. 154(b) by 337 days.

(21) Appl. No.: 16/615,190

(22) PCT Filed: May 21, 2018

(86) PCT No.: PCT/GB2018/051367
§ 371 (c)(1),
(2) Date: Nov. 20, 2019

(87) PCT Pub. No.: WO2018/215742
PCT Pub. Date: Nov. 29, 2018

(65) Prior Publication Data

US 2020/0171698 A1    Jun. 4, 2020

(30) Foreign Application Priority Data

May 20, 2017 (GB) .................................. 1708113

(51) Int. Cl.
| | | |
|---|---|---|
| B27N 1/02 | (2006.01) | |
| B27N 3/00 | (2006.01) | |
| B27N 3/08 | (2006.01) | |
| C09J 105/02 | (2006.01) | |
| C12N 1/16 | (2006.01) | |
| C09J 103/02 | (2006.01) | |
| C09J 11/04 | (2006.01) | |
| C08L 63/00 | (2006.01) | |
| C08L 77/00 | (2006.01) | |

(52) U.S. Cl.
CPC ........... *B27N 1/0209* (2013.01); *B27N 3/002* (2013.01); *B27N 3/08* (2013.01); *C09J 11/04* (2013.01); *C09J 105/02* (2013.01); *C12N 1/16* (2013.01); *C08L 63/00* (2013.01); *C08L 77/00* (2013.01); *C09J 103/02* (2013.01)

(58) Field of Classification Search
CPC ..... C09J 199/00; C09J 2499/00; C08L 97/02; C12N 1/16
See application file for complete search history.

(56) References Cited

U.S. PATENT DOCUMENTS

| | | |
|---|---|---|
| 2005/0130273 A1 | 6/2005 | Versali et al. |
| 2005/0215153 A1 | 9/2005 | Corning |
| 2018/0291244 A1* | 10/2018 | Núñez ................... B27N 3/002 |

FOREIGN PATENT DOCUMENTS

| | | |
|---|---|---|
| CN | 1246508 A | 3/2000 |
| CN | 103254842 A | 8/2013 |
| EP | 0230378 A2 | 7/1987 |
| GB | 2185489 A | 7/1987 |
| JP | S4992308 A | 9/1974 |
| JP | S5324098 A | 3/1978 |
| JP | 62260878 A | 11/1987 |
| JP | 2008024876 A | 2/2008 |
| JP | 2016196162 A | 11/2016 |
| RU | 2404222 C1 | 11/2010 |
| RU | 2493001 C1 | 9/2013 |
| RU | 2642635 C1 | 1/2018 |
| WO | 2014065265 A1 | 5/2014 |

OTHER PUBLICATIONS

Christof Friedrich, Communication pursuant to Article 94(3) EPC, Feb. 26, 2021, European Patent Office, Munich, DE.
Martin Price, UKIPO Patents Act 1977: Search Report under Section 17(5), dated Oct. 17, 2017, UKIPO, Newport, UK.
Christof Friedrich, International Search Report & Written Opinion, dated Jul. 19, 2018, WIPO, Rijswijk, NL.
Yvonne Johnson, Demand, Feb. 7, 2019, Barker Brettell LLP, Birmingham, GB.
Christof Friedrich, Iper, Mar. 20, 2019, WIPO, Rijswijk, NL.
Roman Kollar, et al., Architecture of the Yeast Cell Wall, The Journal of Biological Chemistry, Jul. 11, 1997, pp. 17762-17775, vol. 272, No. 28, Rockville, MD.
Yang Fang, Search Report, dated Oct. 12, 2020, Beijing Center of the Patent Office, CNIPA, China.
Jose Ruiz-Herrera, et al., Cell Wall Glucans of Fungi. A Review, The Cell Surface, Mar. 21, 2019, vol. 5, Elsevier, NL.

* cited by examiner

*Primary Examiner* — Mary Lynn F Theisen
(74) *Attorney, Agent, or Firm* — Kearney, McWilliams & Davis; Erik J. Osterrieder

(57) ABSTRACT

A method for producing a shaped article comprising: a) providing a binder, which has been produced by a process of: (i) mixing (A) fungi or glucan and (B) starch with an alkaline agent to form an alkaline composition; and mixing the alkaline composition with an acidic agent to form the binder; or (ii) mixing (A) fungi or glucan and (B) starch with an acidic agent to form an acidic composition; and mixing the acidic composition with an alkaline agent to form the binder; (b) forming a binder composition by mixing the binder with filler material; (c) shaping the binder composition into a three-dimensional shape; and (d) curing the binder composition to form a shaped article having said three-dimensional shape, wherein steps c) and d) can be carried out simultaneously or separately, and wherein during one or both of steps c) and d) pressure is applied to the binder composition.

30 Claims, 11 Drawing Sheets

BINDER MATERIALS

REFERENCE TO RELATED APPLICATIONS

This is a national entry application from and that claims priority to PCT application PCT/GB18/51367 filed May 21, 2018, which claims priority to GB provisional application number 1708113.4 filed May 20, 2017, and that are incorporated hereby in their entireties.

FIELD

This invention relates to binders and articles formed from binders. The binders are based on fungi or glucan, i.e., one or both of fungi and glucan are used as starting materials, together with starch, e.g., dextrin. The invention provides methods to produce three-dimensional shaped articles from these binders, as well as methods to produce certain such binders and methods to form three-dimensional composite products where component parts are secured together by certain such binders. The shaped articles, composite products and binders can be sustainably sourced and are non-toxic. The shaped articles and composite products have excellent strength characteristics.

BACKGROUND

Engineered wood products are frequently used in the construction industry. These products are made from pieces of wood that are secured together using adhesives and/or binders to produce a composite wood product. Different types of engineered wood products can be manufactured from different wood-based feedstocks, such as strands, fibers, chips or thin layers (plies). Common engineered wood products include particle board, fiberboard, and plywood, e.g., medium-density fiberboard (MDF). Engineered wood products can vary in their structural and/or non-structural properties, and find a variety of uses such as in furniture and construction.

The engineered wood industry has become more sustainable and efficient over time, for example by using wood from replanted forests as a raw material and increasing efficiency through the selection of appropriate types of wood and adhesives or binders.

However, commonly used adhesives and binders in this field are still produced from non-renewable feedstocks. Furthermore, many commonly used adhesives and binders are problematic in terms of their human toxicity and environmental impact.

In the engineered wood industry, the last decade has shown a trend towards the production of non-toxic alternatives formed from sustainable materials.

A particular concern is the amount of formaldehyde present in engineered wood products such as composite wood panel products. Formaldehyde-based resins, such as urea-formaldehyde resins, are used to bind most composite wood products, such as particle board and MDF. In particular, urea formaldehyde is the cheapest binder and is considered to be the most simple to handle. As such, formaldehyde is commonly used in engineered wood used for interior furniture.

Formaldehyde is released into the air, both during the production of composite wood products and during the lifetime of composite wood products. Worryingly, various organizations, such as the National Research Council (US), ECHA (EU) and the International Agency for Research on Cancer IARC (International), have identified formaldehyde as a potential carcinogen and as an irritant.

In 2015, European standards were enacted for engineered wood products, which restricted the lifetime emissions of formaldehyde from engineered wood products. Even tighter restrictions might be enacted in Europe as early as 2019. In the US, strict regulations on the formaldehyde content of engineered wood products were enshrined in federal law in 2017, with new products having to comply with these regulations from 2018.

The amount of formaldehyde released over the lifetime of an engineered wood product is controlled by industry standards. In Europe, engineered wood products are categorized based on their formaldehyde emission grade into categories E0, E1, and E2. Fewer than 15% of online suppliers of MDF are believed to be compliant with the lowest formaldehyde emission grade E0.

Manufacturers in the engineered wood panel industry are actively seeking substitutes for current formaldehyde-based resins. However, formaldehyde within the binder itself is hard to remove completely.

Isocyanate-based binders and adhesives such as pMDI are formaldehyde-free alternatives commonly used in the engineered wood industry. They enable engineered wood articles to be produced that are mechanically very strong, but they are highly toxic before being cured, causing contact dermatitis and becoming particularly hazardous. Therefore use of these isocyanate-based binders and adhesives requires extensive retooling to safely enclose any machine or process unit where the isocyanate-based material is sprayed. In addition, isocyanate-based binders and adhesives are more expensive than UF resins. Furthermore, there have been problems in supplying isocyanate adhesives in sufficient quantities in recent years, due to lack of availability of raw materials.

An approach that is regularly taken is to use formaldehyde-based resins but to add additives and/or coatings that scavenge formaldehyde during the production process and/or to the finished product. However, it will be appreciated that including these additional materials involves an additional cost, making the end products more expensive to manufacture. Meanwhile, scavengers have no significant benefit on the curing time or strength of articles.

The production processes themselves have also been altered to allow for the formaldehyde to outgas in the factory, instead of the formaldehyde being released in the typically confined indoor environments where the engineered wood products find their end use. However, this still necessitates release of formaldehyde into the environment, and makes the production process more complex.

Biologically sourced alternatives to formaldehyde-based binders, such as soy-based binders, have been developed. However, many still fail to act as effective binders or adhesives, producing products that are weaker than required in the engineered wood industry. It will be appreciated that strength is an important factor for many engineered wood products, which find uses in end products such as furniture and structural units.

In addition, binders that been developed to exploit biological resources are often based on resources that not available in quantities that would allow for widespread commercial use.

Some traditional biologically sourced alternatives also have a high viscosity, and therefore water must be added to counteract this so that the binder is usable; it will be appreciated that the binder must be mixed with filler material such as wood chips or sawdust to produce engineered wood products such as chipboard and particleboard. However, the addition of water increases curing time. Therefore, biologically sourced binders and adhesives have typically found only niche application.

Accordingly, it is one object of the present invention to provide binders that can replace or reduce the use of traditional formaldehyde-based resins. A further object of the present invention is to provide binders that are non-toxic and can be prepared from sustainable sources. Articles may be prepared from such binders in combination with other non-toxic and sustainable raw materials, to provide articles that are non-toxic and prepared from sustainable sources.

A further objective of the present invention is to provide binders that have relatively low viscosity, such that they are easy to handle and can be readily mixed with filler material such as wood chips or sawdust, without requiring the addition of amounts of water that would adversely affect curing time.

A further objective of the present invention is to provide binders that can be used to prepare engineered wood products that have good strength characteristics.

SUMMARY

According to a first aspect, the invention provides a method of producing a shaped article as defined in claim 1. The shaped articles made by the first aspect may usefully be engineered wood products, such as particleboard, chipboard or fiberboard (e.g., MDF or insulation board).

In one embodiment it may be that the binder as used in the method has been produced by mixing fungi with an alkaline agent to form an alkaline composition; and mixing the alkaline composition with an acidic agent to form a fungi-based binder having a pH from 5 to 9.

According to a second aspect, the invention provides a method of producing a shaped article which is an engineered wood product, as defined in claim 5. The shaped article made by the second aspect may usefully be plywood.

These methods of the invention are scalable, due to the ease of the manufacturing process and abundance of the raw materials employed. In a preferred embodiment the binder uses fungi, such as yeast or mushrooms, as a key raw material, together with starch. Yeast is cheap and used on a vast scale in both brewing and baking. Spent yeast is readily available. As shown in the Examples, yeast of the type used for animal feed (which may be low-grade yeast), can be employed in the present invention to produce strong engineered wood products. As such, the invention can provide sustainably sourced articles.

The binder as used in these methods of the invention has been determined to have excellent properties in terms of its ability to bind and adhere. When fungi, e.g. yeast, is used as a starting material, the binder has the further benefit of being formed from a natural source material that is readily available, meaning that the binders are able to be produced on a large scale. Thus the invention has the potential to be a widespread commercially viable option, rather than solely a niche solution.

Articles as made by these methods of the invention are advantageously resilient and strong, for example, in terms of their resistance to forces such as compression, and/or in terms of their durability. In particular, articles as made by these methods of the invention are advantageously resilient and strong in terms of their modulus of rupture (MOR), modulus of elasticity (MOE), and in a three-point bending test.

The shaped articles that are made by these methods of the invention are solid, as demonstrated by the examples. Articles in the shape of boards made according to the invention are particularly strong when heat-pressed, and advantageously can be used in the production of items of furniture or structural items.

Shaped articles made by these methods of the invention may be, for example, construction articles, such as insulation boards (such as low-density insulation boards); flooring structures or roofing structures (including tiles, sheets and panels); packaging articles, such as crates, boxes or trays; or furniture articles, such as tables, chairs or stools. However, the invention is not limited to a particular type of article.

The present inventors have determined that the curing time required for the composition is important for efficient industrial application of the present invention. Binders according to the present invention can be cured rapidly, and may achieve curing times of around 10 to 20 seconds per mm of board thickness, e.g. from 12 to 18 seconds per mm of board thickness. This is not dissimilar to the curing times of conventional binders. Furthermore, such curing times are amongst the fastest curing times of any currently available bioadhesive.

A yeast-based adhesive has been described in Kadimaliev et al., BioResources (2012) 7(2), 1984-1993. The adhesive was made by mixing brewer's yeast with either hydrochloric acid or sodium hydroxide. The Kadimaliev et al. paper only describes the use of its yeast derivatives as glues for paper, cardboard or wood—i.e. for holding two such surfaces together. Furthermore, significantly, the Kadimaliev et al. paper only describes products that have been formed by subjecting yeast to treatment with acid or with alkali.

The present inventors have surprisingly found that the treatment of a starting material comprising yeast together with starch with both acid and alkali produces a product that is advantageous as compared to a product that is made using only acid treatment or base treatment. In this regard, the resulting product from a dual treatment has excellent binder characteristics, being able to be easily mixed with filler material (such as wood chips or sawdust) and resulting in unexpectedly strong engineered wood products. In contrast, the resulting product from a single treatment (acid or alkali) cannot usefully be used as a binder because it does not readily mix with filler material (such as wood chips or sawdust) and does not result in strong composite products. This is evidenced in the present Examples.

Meanwhile, the biological field has long recognized that methods comprising stirring yeast with alkali and acid can be used to lyse yeast cells, liberating cellular components. This is described in, for example, Biochem. J. (1966) 101, 36c and Biochem. J. (1937) 81, 72. However, this document does not contemplate any potential commercial uses of the lysed cells; it is focused on examining more highly purified specimens of the cell wall, such as glucans and chitin. Indeed, despite this lysis being described in the 1960s, no commercial use for the lysed cells has apparently been determined to date.

Further, the techniques used to lyse yeast cells in the prior art in the biological field are different to the preferred conditions used in the methods of the present invention. In particular, the prior techniques had the intended aim to study materials, meaning that it was desired to keep cell materials intact and minimize denaturing of protein materials.

US 2005/0130273 describes methods for isolating cell wall derivatives from fungal or yeast biomass, in particular using *Aspergillus niger* biomass. These methods are focused on the isolation of chitin and preparing chitin polymers and chitosan that are not animal derived. The methods are used to produce products such as hydrogels, films and porous objects. The end uses are in areas such as healthcare, cosmetics, and food. Although the methods use an alkali treatment and an acid treatment, it is described as essential to discard the alkali-soluble fraction before adding the acid. Therefore only an extract undergoes the treatment, rather than the fungal/yeast biomass undergoing both an acid and an alkali treatment as in the present invention.

JP S49-92308 describes the manufacture of a composition for use as a paper coating that improves the gloss of that paper. The coating is applied to the paper and allowed to dry. The binding agent used within the coating is obtained from yeast (Pichia miso biomass) in wet form, as a cleansing milk having a bacterial cell concentration of approximately 10 wt %. Although the methods of producing the binding agent use an alkali treatment and an acid treatment, after the alkali treatment the residue was separated by centrifugation and removed, and then acid was added, and then precipitated proteins were separated and recovered by a centrifuge. Therefore only an extract undergoes the treatment, rather than the yeast undergoing both an acid and an alkali treatment as in the present invention.

JP S53-24098 also describes the manufacture of a composition for use as a paper coating. The coating is applied to the paper and allowed to dry. The binding agent used within the coating is obtained by adding alkali to a microorganism to bring the pH to 10 to 16, as well as adding a surfactant, and heating, before then adding acid to adjust the pH to 3 to 5, so as to precipitate out a complex of protein and surfactant. It is this white powder precipitate as obtained by separation which is then used in the coating composition, i.e. an extract rather than the whole treated product.

RU 2404222 describes adhesives made from brewer's yeast, boric acid and sodium hydroxide. The adhesive is described as being useful for gluing. To obtain the adhesive yeast is treated with sodium hydroxide in a 1:1 ratio and this is then combined with boric acid and glycerin. The boric acid is used in amounts of 0.1-0.3% with the amount of alkali-treated yeast sediment being 96.0-98.0%.

GB 2 185 489 describes adhesives made by treating yeast with alkali and optionally also with acetic acid. The adhesive is described as being useful for bonding two adjacent surfaces.

WO2017/075725 describes a process of preparing a yeast extract, which is used to make particleboards. The document describes that yeast cells were thermally lysed, before proteins were isolated from the yeast using centrifugation, an energy intensive step. The protein isolate was used to make particle board. In this regard, a 10 mm thick particleboard was cured in a time of 24 seconds/mm of board thickness. Alkali and acid treatment of the yeast is not described; the treatment used is thermal and is designed to obtain a protein isolate which is then the only component of the yeast used.

The present inventors have surprisingly found that binders can be obtained from fungi (such as yeast or mushrooms) or glucan (such as beta glucan), together with starch (such as dextrin), which are highly effective at forming shaped articles, especially sheets or panels or tiles, which are strong, resilient and versatile. These binders are obtained by a treatment with both alkali and acid. This combination of starting materials and treatments is new and is surprisingly effective.

Whilst products formed from acid and/or base treatment of biomass have been formed before, these were used as binding agents in coating compositions, or as standard adhesives. These are not binders.

As the skilled person will appreciate, a binder is a substance that can be blended or mixed with another material in the form of particles or other pieces and that, once cured, serves to hold them together to form a shaped cohesive whole. The characteristics of an effective binder are therefore not identical to those of an adhesive or a binding agent in a coating composition. A binder must be able to be readily blended or mixed with another material in the form of particles or other pieces. A binder must be able to cure to give three-dimensional strength, so as to provide a useful composite product where the combined binder and filler material are held together to provide a strong and resilient shaped article.

The most common thickness of particleboard is 18 mm, and the thicker the board is the more difficult it is to cure the core. The present invention can be used to produce particleboards that are 18 mm thick and that are cured in about 10-20 seconds/mm of thickness, e.g. 12-18 seconds/mm of thickness. The ability to produce boards thicker than 10 mm and with fast curing speeds when using a non-toxic binder is a significant technical advance provided by the present invention.

The binders as provided by the present invention cure to give an unexpectedly strong composite product. The shaped articles provided in accordance with the present invention have a surprisingly high modulus of rupture and modulus of elasticity. The binders as provided by the present invention also have a low viscosity relative to their solid content. The binders as provided by the present invention mix well with filler material (such as wood chips, sawdust or wood fibers). The low viscosity of the binders as provided by the present invention means that the binder can have a relatively low water content, allowing the binder to cure quickly by evaporating water whilst also enabling facile mixing with filler material. The binders as provided by the present invention have a short curing time, particularly when cured by hot pressing. These advantageous technical effects are shown in the Examples section.

A further benefit is that products made using the binder have water resistance that is sufficient for indoor applications. Thickness swelling and water absorption of particleboards made according to the invention and soaked 24 hours in water were similar to the performance of urea-formaldehyde. This is shown in the Examples.

Furthermore, the articles provided by the present invention are not toxic to human health and are environmentally benign in part due to their low or non-existent formaldehyde and/or VOC content.

Additionally, the fungi feedstock is environmentally friendly and comes from a renewable source.

The binder of the present invention can also easily be integrated into existing manufacturing processes within the engineered wood industry to partially or fully replace existing urea-formaldehyde resins. Thus products such as particle board can usefully be made using the present invention. However, it will also be appreciated that the benefits and uses of the binder of the present invention are applicable in fields beyond the engineered wood industry.

The combination of excellent strength together with the ability to have a non-toxic product and the ability to use naturally sourced starting material means that there are many potential end uses for the invention, including in furniture, construction and packaging.

According to a third aspect, the invention provides an article obtainable by the method of the first or second aspect.

The inventors have surprisingly found that articles as made by the methods of the invention have beneficial characteristics. As discussed above, the binder imparts excellent mechanical and chemical properties to the article as formed. The article may, in particular, be resilient and strong.

In the present invention, there is a combination of both alkali treatment and acid treatment of fungi (such as yeast or mushrooms) or glucan (such as beta glucan) together with the use of a starch, such as dextrin. This combination has been found to lead to new products which have excellent characteristics for use as a binder.

Therefore, according to a fourth aspect, the invention provides a method to prepare a binder, comprising the steps of:
 i. mixing (A) fungi or glucan and (B) starch with an alkaline agent to form an alkaline composition; and mixing the alkaline composition with an acidic agent to form the binder; or
 ii. mixing (A) fungi or glucan and (B) starch with an acidic agent to form an acidic composition; and mixing the acidic composition with an alkaline agent to form the binder.

It may be that the alkaline agent is provided as an aqueous solution of an alkali which has a pKaH of 8 or more, such as 11 or more, and with the alkali concentration being 10% or more by weight of the alkaline agent. It may be that the acidic agent is provided as an aqueous solution of an acid which has a pKa of 5 or less, such as 2 or less, and with the acid concentration being 10% or more by weight of the acidic agent.

The quantities of alkaline agent and acidic agent are suitably selected such that the resulting binder has a pH from 5 to 9, e.g. from 5.5 to 8 or from 6 to 8. In other words, the alkaline agent and acidic agent preferably substantially neutralise each other.

In some embodiments of the present invention relatively strong acids and strong alkalis are added to the fungi/glucan and starch starting material, and in relatively high concentrations, to provide strong and effective binders that have a relatively low viscosity, and to reduce the amount of water to be removed in the curing stage.

The binders as formed in the present invention can be used in relatively low proportions as compared to the amount of filler material (e.g. woodchips or sawdust) in the three-dimensional shaped composite product, reflecting their excellent structural characteristics. This is shown in the Examples.

According to a fifth aspect, the invention provides a binder obtainable by the method of the fourth aspect.

The binder has good binding properties and good adhesive properties. It can therefore be (I) used as a binder, specifically to form three dimensional shaped articles from cured binder, wherein these articles have component parts (e.g. woodchips or sawdust) dispersed through the cured binder; and (II) used as an adhesive, to secure two surfaces together (e.g. it can be used as a label adhesive).

It will be appreciated that in some embodiments of the first or second aspects, the binder is in accordance with the fifth aspect or is formed by the method of the fourth aspect.

As stated above, the inventors have also determined that the binders of the present invention provide excellent adhesion between two surfaces.

Therefore, according to a sixth aspect, the invention provides a method of securing two component parts together to produce a composite product, each component part having a contact surface, the method comprising:

a) providing a binder according to the fifth aspect;
b) applying the binder to the contact surface of the first component part and/or the contact surface of the second component part;
c) bringing together the contact surface of the first component part and the contact surface of the second component part; and
d) curing the binder to secure the two component parts together, to produce the composite product.

It will be appreciated that the two component parts are therefore secured together by adhesion at their contact surfaces.

Composite products as made by this method of the invention have been found to have better joint strength than composite products formed using conventional adhesives, for example being able to withstand almost twice the load before the joint fails.

In one embodiment step a) comprises carrying out the method of the fourth aspect.

Pressure may be applied during step c) and/or step d) to assist with the securing of the two components together.

According to a seventh aspect, the invention provides a composite product obtainable by the method of the sixth aspect.

As noted above, the present invention provides binders that have surprisingly good adhesive characteristics. It is believed that the use of the specific alkaline and acid treatments gives rise to these characteristics. The treatments are believed to provide an effective breaking down of the fungi cell walls and then re-linking of hydrolyzed material from the fungi cells, which occurs under substantially neutral conditions. The inclusion of starch, e.g. dextrin, together with the fungi leads to excellent strength characteristics in the end product.

In one embodiment the composite product is a wood-based product. In another embodiment the composite product is a container (e.g. a bottle or jar) and a label which are secured together, to form a labelled container.

In all aspects of the invention, it can be preferable for a crosslinker, e.g. PAE, to be included in the binder as well. This improves the properties of the binder, as discussed in more detail below and as shown in the Examples.

In all aspects of the invention, the starting material comprising (A) fungi or glucan and (B) starch is preferably provided in the form of an aqueous mixture before the alkali and acid treatment. In one embodiment, the aqueous mixture has a water content of from 45 to 90 wt %, such as from 50 to 80 wt % or from 50 to 70 wt %. In other words, the dry content (the content that is not water) of the starting material before the alkali and acid treatment may suitably be from 10% to 55%, by weight, such as from 20 to 50% by weight or from 30% to 50% by weight.

BRIEF DESCRIPTION OF THE DRAWINGS

So that the manner in which the above recited features, advantages and objects of this disclosure are attained and may be understood in detail, a more particular description, briefly summarized above, may be had by reference to the embodiments thereof which are illustrated in the appended drawings.

It is to be noted, however, that the appended drawings illustrate only typical embodiments of this disclosure and are therefore not to be considered limiting of its scope, for the disclosure may admit to other equally effective embodiments.

FIG. 7 depicts a boxplot showing results of when acid and alkali are used to produce binders in accordance with this disclosure.

DETAILED DESCRIPTION

Figures 1A, 1B:
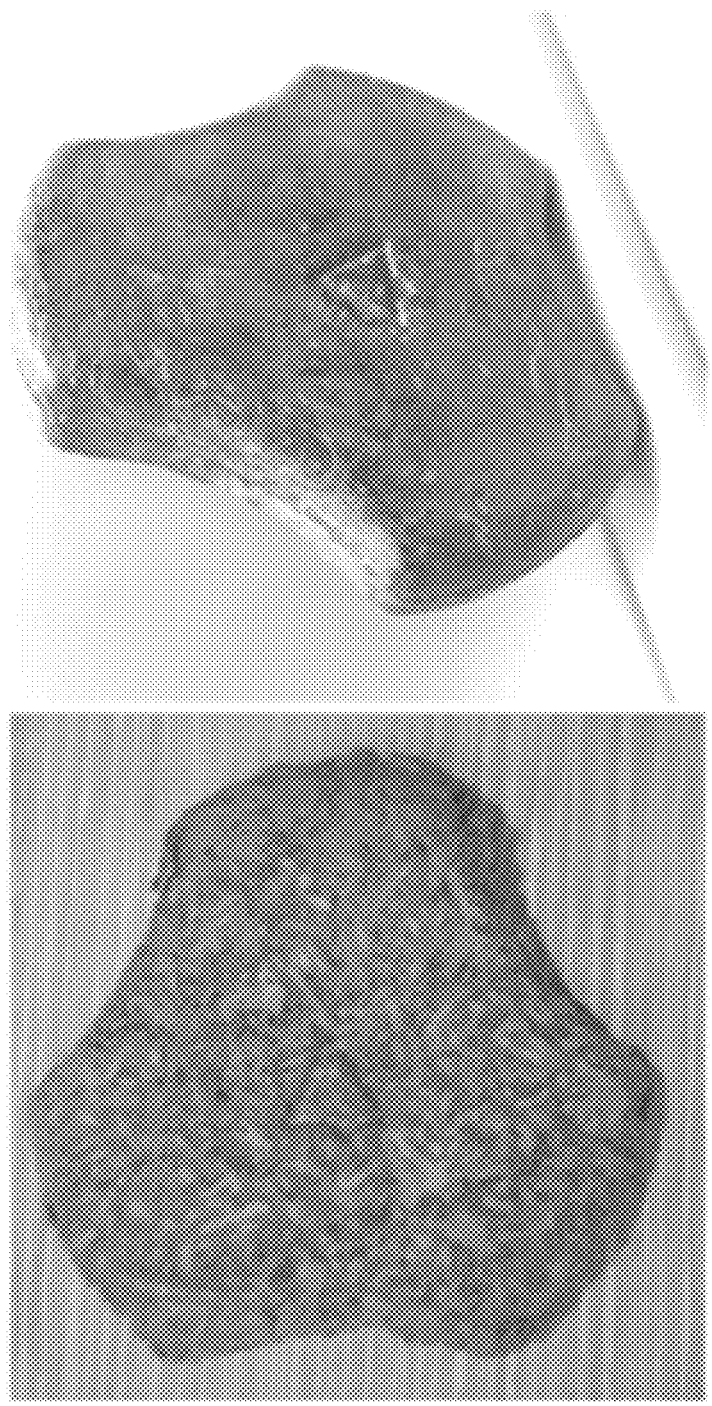
FIGS. 1a-1d depict tiles in accordance with this disclosure.
Figure 1D:
Figure 1C:
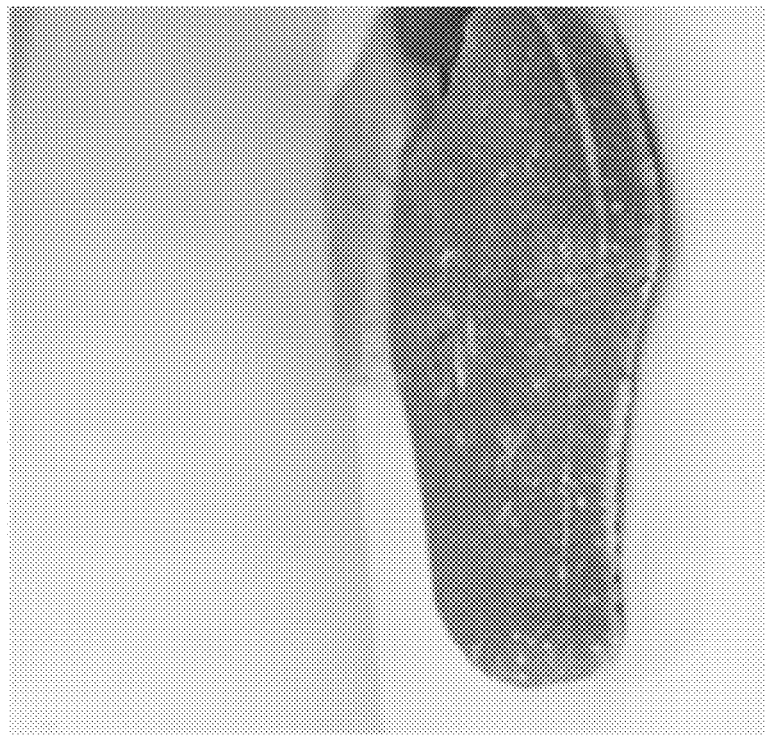
Figure 1F:
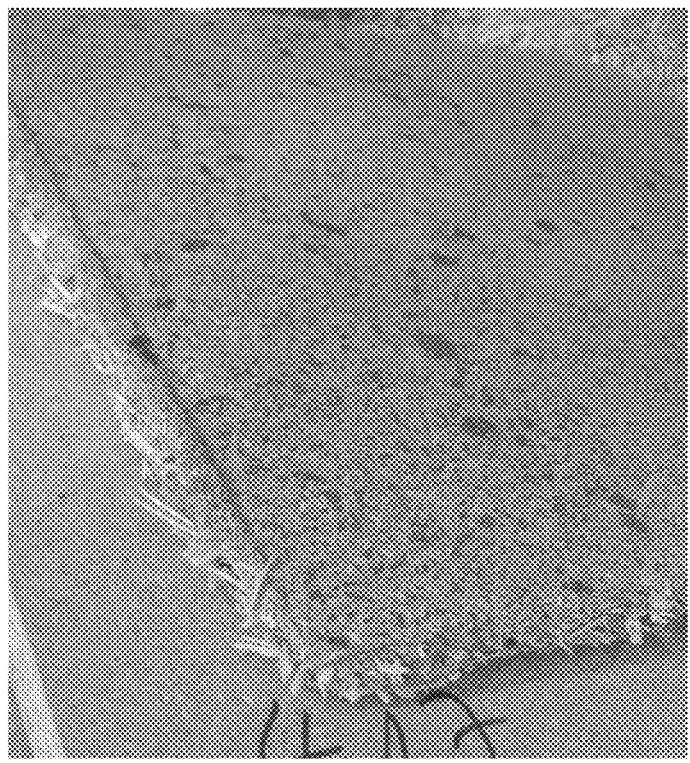
FIG. 1f depicts a particle board panel in accordance with this disclosure.

In the present invention a binder can be made, and a shaped article can be formed from a binder, and a composite product can be made using a binder. The binder may be a fungi-based binder, i.e., it is made using fungi as a starting material, or it may be made using glucan (e.g., beta glucan) as a starting material. All optional embodiments and disclosed features within the following description apply to all aspects of the invention except where contradictory with the definition of a given aspect as provided in the above Summary of the Invention.

The binder can be produced by mixing (A) fungi (e.g. yeast) or glucan (e.g. beta glucan) and (B) starch with an alkaline agent and then subsequently with an acidic agent, or vice versa.

The present inventors have determined that a useful binder can be formed from a natural source material, namely fungi. Particularly suitable fungi include those capable of forming biofilms and/or colonies. Fungi that contain glucans, such as beta glucans, are especially suitable for use in the present invention.

Examples of fungi that may be contemplated for use include, but are not limited to, species of the *Saccharomyces* genus, species of the *Candida* genus, *Cryptococcus neoformans*, species of the *Trichosporon* genus, and species of the *Aspergillus* genus, such as *Aspergillus fumigatus* and *Aspergillus niger*. Other examples that can be mentioned included those of the genus *Penicillium*, the fungus *Trychoderma*, *Aspergillus oryzae* and *Fusarium venenatum*. In one embodiment the fungi may be *Saccharomyces cerevisiae*, *Saccharomyces boulardi*, *Saccharomyces uvarum*, *Candida albicans*, *Candida glabrata*, *Candida parapsilosis*, *Candida dubiliensis*, *Candida tropicalis*, or *Trichosporon asahi*.

In one embodiment the fungi may be *Lentinula edodes* (shiitake mushroom), *Trametes versicolor* (turkey's tail mushroom), *Inonotus obliquus* (chaga mushroom) or *Hericium erinaceus* (lion's mane mushroom). These fungi are not yeasts but, as shown by the examples, have been shown to produce effective binders. When using non-powdered fungi, such as mushrooms, it may be necessary to grind the fungi into a powder prior to treating with the alkali.

The fungi may be a Dikarya. In one embodiment the fungi is in the phylum Ascomycota. In one preferred embodiment the fungi is a yeast. In one embodiment the fungi is selected from wild yeasts, such as *Pichia*, *Kloeckera*, and *Torulopsis*. In another embodiment the fungi is a yeast of the *Saccharomyces* genus.

The yeast is suitably *Saccharomyces cerevisiae* yeast, especially of the baker's yeast strain. In one preferred embodiment the yeast is brewer's yeast, such as spent brewer's yeast, or baker's yeast. However, other forms of yeast could be contemplated.

Preferably the yeast is sourced from baker's yeast, or from brewer's yeast (such as spent brewer's yeast), or it may be yeast of the type used for animal feed (which may be low-grade yeast). Baker's yeast may be sourced from Lallemand (Fermipan); low-grade yeast may be sourced from Cangzhou Xindewei Animal Drug Co.; and spent brewer's yeast may be sourced from the brewing process. Yeast that is typically used in animal feed typically contains about 40-60% by weight of a mixture of *Candida* and *Saccharomyces* yeast, and other components such as ashes.

The yeast may be in a dry powdered form or may be a by-product of the brewing process. In dry powdered form, yeast has a typical water content of around 4% by weight, such as 2-8 wt %, whereas spent brewer's yeast has a typical water content of 10-70 wt %.

In the case of spent brewer's yeast, before the yeast is used to make the binder its water content may be decreased. This may suitably be achieved using air drying, oven drying, or a centrifuge. The use of high temperatures, such as above 40° C., may denature and/or destroy useful cell wall biomolecules. Therefore preferably the drying is achieved at 40° C. or below, e.g. at about room temperature. The use of a centrifuge at, for example 1000-5000 (e.g. about 3000) revolutions per minute for a period of time from 1 to 30 minutes (e.g. about 10 minutes) may be suitable.

In general, it is preferable that the fungi in the form as used to make the binder has a water content of 25 wt % or less, e.g. 20 wt % or less or 15 wt % or less, such as 10 wt % or less. In one embodiment it has a water content of from 0.5 to 20 wt %, e.g. from 1 to 15 wt % or from 2 to 10 wt %.

As the skilled person will appreciate, the moisture content may be determined by measuring the electrical conductivity, at 20° C. and atmospheric pressure, using a conductive sensor. A conductive sensor uses two electrodes inserted directly into the material to measure its conductivity. The sensor can determine the material's moisture content from this measurement because each material has a specific conductivity that changes based on its moisture content.

As an alternative to fungi, glucan, e.g., beta glucan, can be used as the starting material. The Examples show that the use of fungi and the use of glucan both lead to excellent results in terms of the properties of the end product. However, fungi, e.g. yeast, may be preferred as the starting material due to the fact it is a natural source material and is readily available. In the case of materials such as spent brewer's yeast or baker's yeast the material is also low cost.

Beta glucan can be sourced commercially, e.g., from Naturheilpraxid Bedarf, Germany.

The glucan, e.g. beta glucan, can suitably have a water content of up to 10 wt %, e.g. from 1 to 7 wt % or from 2 to 6 wt %, such as from 3 to 5 wt %.

The starting material used in the present invention comprises the fungi, e.g., yeast, or the glucan, e.g. beta glucan, in combination with starch.

In this regard, a starch, such as dextrin or another modified starch, is provided in combination with the fungi or glucan before the treatment with alkaline agent and acidic acid is carried out. The starch and the fungi or glucan may be mixed together before the treatment with alkaline agent and acidic acid is carried out. The inclusion of the starch as a starting material is thought to be important because it means that the starch is alkalised. This means that it forms a better macromolecular structure with the glucans of the yeast. Therefore the resulting binder has an increased binding strength. If the starch, such as dextrin or another modified starch, is added after the treatment with alkaline agent and acidic acid is carried out then the resulting product is hard to mix and furthermore shaped articles formed from the cured product are less strong.

The type of starch used is not particularly limited. Examples of starch materials that can be contemplated for use include: modified starches; cationic starches; carboxymethyl starches; oxidised starches; bleached starches; and monostarch and distarch phosphates. Acetylated starches can have high viscosity, but could still be contemplated, especially for surface applications, e.g. in the method of the second aspect of the invention and/or of the sixth aspect of the invention. Likewise, hydroxypropyl starches can increase viscosity, but are very strong and could certainly be contemplated especially for surface applications, e.g., in the method of the second aspect of the invention and/or of the sixth aspect of the invention.

Preferably the starch is selected from: dextrin or other modified starches, amylose, amylopectin and maltodextrin. More preferably the starch is dextrin.

Whilst starches, such as dextrin, have found application within the paper and pulp industries, the engineered wood industry has not yet found a use for starches, such as dextrin, as they do not possess sufficient binding characteristics.

However, the present inventors have surprisingly found that when the articles of the present invention are made without a starch as a starting material, the articles are inferior in terms of their strength, as measured by the modulus of rupture.

In particular, dextrin has been shown to be particularly effective in increasing the strength of articles provided by the methods of the present invention. Dextrins are low molecular weight forms of starch that are refined with a simple process from starch. In particular, dextrins can be produced by the hydrolysis of starch or glycogen. Dextrins can be produced from starch using enzymes such as amylases, or by applying dry heat under acidic conditions (pyrolysis or roasting). Dextrins are mixtures of polymers of D-glucose units linked by α-(1→4) or α-(1→6) glycosidic bonds.

The dry starting materials, namely the fungi or the glucan in combination with the starch, preferably includes the starch, such as dextrin, in an amount of up to 50% by weight, e.g. up to 40% by weight, such as from 0.01% to 50%, or 0.01% to 40%, such as 0.1% to 20%, or 0.5% to 15%, or 0.5% to 10%, or 1% to 10%, or 1% to 5% by weight.

Preferably the starch is included in an amount of 0.5 to 15% by weight, such as from 0.5% to 10% by weight.

In the starting material, there may suitably be a weight ratio, when considering the dry materials, of fungi/glucan to starch of from 200:1 to 1:1, such as from 200:1 to 5:2 or from 200:1 to 6:1 or from 200:1 to 10:1; in one embodiment the ratio may be from 100:1 to 1:1, such as from 100:1 to 5:2 or from 100:1 to 6:1 or from 100:1 to 10:1. It may be that the ratio is from 75:1 to 1:1 or from 50:1 to 1:1. In one embodiment, there may be a weight ratio, when considering the dry materials, of fungi/glucan to starch of from 100:1 to 3:2, such as from 75:1 to 3:2 or from 50:1 to 3:2. In another embodiment, there may be a weight ratio, when considering the dry materials, of fungi/glucan to starch of from 100:1 to 2:1, such as from 75:1 to 2:1 or from 50:1 to 2:1.

Dextrin can be sourced from sourced from Atlantis Art Materials. Typically, the dextrin will be added as a dry powder. This may suitably have a moisture content of from 1 to 10% by weight, e.g. from 1 to 5% by weight.

Without being bound by theory, it is thought that the present invention works by releasing fungal cell wall components, such as glucans, mannans and/or chitins, which bind well to filler materials, especially wood-based filler materials. The alkaline agent interacts with the fungi to lyse the fungi cell walls. This process is exothermic. It is thought that both the chemical action of the alkaline agent and the heat produced by the interaction of the fungi with alkaline agent aid the hydrolysis of the fungi cell walls. It is believed that the fungi cell walls are shrunk and opened by this process, allowing their structure to become unbound. Glucan, mannan and/or chitin layer polysaccharides are thought to be liberated in this process.

The starting material comprising (A) fungi or glucan and (B) starch is preferably provided in the form of an aqueous mixture before the alkali and acid treatment. In one embodiment, the aqueous mixture has a water content of from 45 to 90 wt %, such as from 50 to 80 wt % or from 50 to 70 wt %. In other words, the dry content (the content that is not water) of the starting material before the alkali and acid treatment may suitably be from 10% to 55%, by weight, such as from 20 to 50% by weight or from 30% to 50% by weight.

Therefore, the (A) fungi or glucan and/or (B) starch may optionally be diluted with water before the alkali and acid treatment. In this regard, water may be added to the (A) fungi or glucan and/or (B) starch such that the starting material comprising (A) fungi or glucan and (B) starch, at the point before the alkali and acid treatment is started, has a water content of from 45 to 90 wt %, such as from 50 to 80 wt % or from 50 to 70 wt %.

The process for preparing the binder may suitably be carried out at a temperature of from room temperature up to 80° C., preferably from room temperature up to 45° C.

It is advantageous, but not essential, that the fungi is first treated with alkaline agent, before being treated with acidic agent.

However, as shown in the Examples, good results are also obtained when the acid treatment is carried out first, followed by alkali treatment. What has been shown to be important is that there is both an alkali treatment and an acid treatment, and that the starting material includes starch as well as fungi (or glucan).

It is preferable that the alkaline agent is provided as an aqueous solution; this permits good control of its reaction with the fungi. In one embodiment the alkaline agent is provided as an aqueous solution with an alkali concentration of from 1% to 80% by weight, such as 1% to 70% by weight, or 1 to 60% by weight, or 2% to 50% by weight, such as from 5 to 45% by weight. In a preferred embodiment, the alkaline agent is provided as an aqueous solution with an alkali concentration of 10% or more, such as 15% or more, or 20% or more, or 40% or more by weight; e.g. from 30% to 70% by weight, or 50% to 70% by weight, or 55% to 65% by weight; or it may be from 10% to 60% by weight, or from 10% to 50% by weight, or from 15% to 45 wt % or from 20% to 40% by weight. In one embodiment, the solvent is water, such as tap water.

The alkaline agent should be strong enough to lyse the fungi cell walls. In one embodiment, the alkali used in the alkaline agent has a pKaH (pKa of its protonated form) of 9 or greater, such as 10 or greater. Preferably, the alkali has a pKaH of 11 or greater, such as 12 or greater, or 13 or greater. Such alkalis have been found to give good results.

As the skilled person will appreciate, pKa values for acids are known in the art. These can also be determined by the Henderson-Hasselbalch equation, which relates pH and pKa to the equilibrium concentrations of dissociated acid [A−] and non-dissociated acid [HA] respectively:

$$pH = pKa + \log([A-]/[HA]).$$

The pKaH is the pKa of the conjugate acid for the alkali in question. It will be understood that it is normal to measure pKa and pKaH values in water.

The alkaline agent may be ammonium hydroxide. In one embodiment the alkaline agent is an aqueous solution of an alkali metal or alkali earth metal hydroxide, sulfate, carbonate or phosphate. In a preferred embodiment the alkaline agent is an aqueous solution of an alkali metal or an alkali earth metal hydroxide. In a particularly preferred embodiment, the alkaline agent is an aqueous solution of sodium hydroxide, potassium hydroxide, rubidium hydroxide, caesium hydroxide, calcium hydroxide or strontium hydroxide; e.g. it may be an aqueous solution of sodium hydroxide or potassium hydroxide. In the most preferred embodiment, the alkaline agent is an aqueous solution of sodium hydroxide. Sodium hydroxide and potassium hydroxide are both preferred for their solubility, but sodium hydroxide is yet more preferred as it is cheaper, more readily available and reacts less exothermically than potassium hydroxide.

In one embodiment the alkaline composition has a pH of from 9 to 14, such as from 10 to 13. Preferably the alkaline composition has a pH of from 11 to 12.

The ratio of alkaline agent to fungi/glucan, by weight, may be from 5:1 to 1:100, or from 4:1 to 1:100, or from 2:1 to 1:100 or from 1:1 to 1:50, such as from 1:1 to 1:30 or from 1:1 to 1:20. In a preferred embodiment it is from 5:1 to 1:15, such as from 4:1 to 1:15 or from 3:1 to 1:15 or from 2:1 to 1:15; it may be from 5:1 to 1:10, such as from 4:1 to 1:10 or from 3:1 to 1:10 or from 2:1 to 1:10. In one embodiment it may be from 1:1 to 1:10, e.g. from 1:1 to 1:4, or from 1:1 to 1:3, or from 1:1 to 1:2. It may be that the ratio of alkaline agent to fungi/glucan, by weight, is from 1:2 to 1:15, or from 1:3 to 1:10, such as from 1:4 to 1:10. However, in one embodiment the amount of alkaline agent is from 0.5 to 3 times the amount of fungi/glucan, by weight, such as from 1 to 3 times or from 1 to 2 times. The reference to weights in this regard is in relation to the alkaline agent in the form as actually mixed with the fungi/glucan and starch starting material, i.e. it includes the alkali and any solvent (e.g. water) in which the alkali is diluted, but it does not include any solvent (e.g. water) in the fungi/glucan and starch starting material. As noted above, the alkaline agent is preferably provided as alkali in aqueous solution. The amount of fungi/glucan is the dry weight amount as present in the fungi/glucan and starch starting material.

Preferably the amount of fungi/glucan (e.g. yeast) is equal to or greater than the amount of alkaline agent, such as from 2 to 15 times greater, e.g. from 3 to 10 times greater.

The use of these ratios has been found to give good results in terms of the control of the process and the characteristics of the binder obtained.

Typically, the alkaline agent may be in contact with the fungi/glucan and starch for a period of from 1 minute to 3 hours, or from 1 minute to 2 hours, such as from 2 to 90 minutes, for example from 5 minutes to 1 hour or from 10 minutes to 45 minutes. In one embodiment, the alkaline agent is in contact with the fungi/glucan and starch for a period of from 10 to 30 minutes such as 15 to 20 minutes, or from 20 minutes to 2 hours, or from 60 minutes to 2 hours. Preferably, the alkaline agent is in contact with the fungi/glucan and starch for a period of from 2 to 90 minutes, e.g. from 2 to 60 minutes such as from 2 to 30 minutes or from 2 to 15 minutes. However, longer times are also contemplated, e.g. up to 4 hours or up to 5 hours.

In general, the alkaline agent should be in contact with the fungi/glucan and starch for a period of time long enough to allow the majority of the fungi/glucan to dissolve or lyse. During this alkaline treatment process vapour emissions may occur. Thus the alkaline agent and fungi/glucan and starch can be left until there is a decrease in the vapour emissions. This can be assessed visually or can be automated. Equally, during the alkaline treatment process heat is generated. Thus the temperature can be monitored and the alkaline agent and fungi/glucan and starch can be left until the temperature starts to return to room temperature. This can be assessed manually with a thermometer or can be automated.

It may be that the alkaline agent is mixed with the fungi/glucan and starch during the full period of time they are in contact, or it may be that some of the contact time is at rest. For example, mixing may occur during from 10 to 100% of the contact time, e.g. from 50 to 100% or from 75% to 100% of the contact time. Thus mixing occurs during some, most or all of the contact time period. Carrying out mixing allows the alkaline agent to efficiently react with the fungi/glucan and starch. The mixing is preferably even and steady.

The mixing of the alkaline agent with the fungi/glucan and starch may be carried out using any suitable mixing apparatus. The skilled person will appreciate that the viscosity of the composition should be taken into account in selecting a suitable apparatus. In one embodiment it is performed with a mechanical mixer, such as a planetary mixer or a pan type mixer or a conical screw mixer. It will be appreciated that the speed of mixing may be selected according to the scale of the process and the type of mixing apparatus. The mixing may, for example, be carried out at a speed in the range of from 10 to 1600 rpm. In one embodiment the mixing is carried out with a mechanical paddle at from 10 to 800 rpm, e.g. from 20 to 700 rpm, such as about 40 to 600 rpm. In another embodiment the mixing is carried out with a mechanical paddle at from 50 to 200 rpm, such as from 80 to 140 rpm, e.g. from 100 to 120 rpm. The present invention is not limited to a particular range of mixing speeds and these are purely exemplary. What is important is that, at the scale involved, the mixing speed is selected so as to produce an even, smooth blending of the product.

The mixing may suitably be carried out at around room temperature, e.g. from 15 to 25° C. For example, in one embodiment there is no external heat added. As noted above, the reaction is exothermic. In another embodiment, the mixing is carried out at above room temperature, i.e. above 15° C., and in particular above 25° C., such as above 25° C. and up to 90° C., or from 30° C. to 70° C., e.g. from 40° C. to 60° C.

The mixing may suitably be carried out at around atmospheric pressure. For example, in one embodiment there is no external pressure applied.

Like the alkaline agent, the acidic agent can also interact with the fungi to lyse the fungi cell walls. This process is exothermic.

The acid cleaves the bonds of cell wall components, such as acid-soluble glucans, mannans and/or chitins, which have not been broken down during the alkali phase. The addition of acid also significantly reduces the viscosity of the composition, thereby allowing the binder to flow out of the reaction vessel. It is believed that this reduction in viscosity is due to the acid breaking down the cell wall components into smaller polysaccharides.

If added second, the acidic agent neutralizes the alkaline composition, which further releases glucans from the fungi cell walls. It will be appreciated that if the acidic agent is added first, then the alkaline agent neutralizes the acidic composition, which further releases glucan polysaccharides from the fungi cell walls. The neutralization is exothermic.

It is preferable that the acidic agent is provided as an aqueous solution; this permits good control of its reaction with the fungi/glucan. In one embodiment the acidic agent is provided as an aqueous solution with a concentration of acid of from 2% to 50% by weight, such as from 5 to 45% by weight. In a preferred embodiment, the acidic agent is provided as an aqueous solution with a concentration of acid of 10% or more, such as 15% or more, or 20% or more, by weight. For example, the acidic agent may be provided as an aqueous solution with a concentration of acid from 10% to 50% by weight, or from 10% to 20% by weight, or from 15% to 45 wt %, or from 20% to 40% by weight. In one embodiment, the acidic agent may be provided as an aqueous solution with a concentration of acid from 5% to 30% by weight, or from 5% to 25% by weight, or from 5% to 20 wt %, e.g. from 10% to 20% or from 10% to 15% by weight In one embodiment, the solvent is water, such as tap water.

It will be understood that the term "acid" refers to Brønsted acids. In one embodiment, the acid in the acidic agent has a pKa of 5 or less, or 4 or less, or 3 or less, or 2 or less. Preferably, the acid has a pKa of 1 or less, such as 0 or less.

In one embodiment the acidic agent is selected from an aqueous solution of hydrochloric acid, hydrobromic acid, hydroiodic acid, nitric acid, sulfuric acid, phosphoric acid, carbonic acid, citric acid, lactic acid, maleic acid, formic acid, acetic acid, propionic acid, butyric acid, valeric acid, caprolic acid, oxalic acid, malic acid and benzoic acid.

In one embodiment the acidic agent is selected from an aqueous solution of hydrochloric acid, sulfuric acid, nitric acid, phosphoric acid, carbonic acid, citric acid, lactic acid, formic acid and acetic acid, e.g. it may be selected from an aqueous solution of hydrochloric acid, sulfuric acid, phosphoric acid and nitric acid. In a preferred embodiment, the acidic agent is selected from an aqueous solution of hydrochloric acid, carbonic acid and citric acid. In a more preferred embodiment, the acidic agent is an aqueous solution of hydrochloric acid.

The ratio of acidic agent to fungi/glucan, by weight, may be from 5:1 to 1:15, such as from 4:1 to 1:15 or from 3:1 to 1:15 or from 2:1 to 1:15 or from 1:1 to 1:15. In one embodiment the ratio of acidic agent to fungi/glucan, by weight, may be from 5:1 to 1:10, such as from 4:1 to 1:10 or from 3:1 to 1:10 or from 2:1 to 1:10 or from 1:1 to 1:10. It may be that the ratio is from 4:1 to 1:6, e.g. from 4:1 to 1:4, or from 3:1 to 1:3, such as from 2:1 to 1:2. In one embodiment the ratio of acidic agent to fungi/glucan, by weight, is from 1:2 to 1:6, for example from 1:3 to 1:5, such as about 1:4. In one embodiment the amount of acidic agent is from 0.5 to 3 times the amount of fungi/glucan, by weight, such as from 1 to 3 times or from 1 to 2 times. The reference to weights in this regard is in relation to the acidic agent in the form as actually mixed with the fungi/glucan and starch starting material, i.e. it includes the acid and any solvent (e.g. water) in which the acid is diluted, but it does not include any solvent (e.g. water) in the fungi/glucan and starch starting material. As noted above, the acidic agent is preferably provided as acid in aqueous solution. The amount of fungi/glucan is the dry weight amount as present in the fungi/glucan and starch starting material.

The use of these amounts of acidic agent and fungi/glucan has been found to give good results in terms of the control of the process and the characteristics of the binder obtained.

Typically, the acidic agent may be in contact with the fungi/glucan for a period of from 1 minute to 2 hours, for example from 5 minutes to 1 hour, or from 10 minutes to 1 hour, or from 10 minutes to 45 minutes. In one embodiment, the acidic agent is in contact with the fungi/glucan for a period of from 10 to 30 minutes, such as 15 to 20 minutes. Preferably, the acidic agent is in contact with the fungi/glucan for a period of from 1 to 60 minutes to allow for even blending of the acid into the paste. In one embodiment, the acidic agent is in contact with the fungi/glucan for a period of 1 minute or more, or 2 minutes or more. In one embodiment, the acidic agent is in contact with the fungi/glucan for a period of 1 hour to 2 hours. However, longer times are also contemplated, e.g. up to 4 hours.

If added second, the acidic agent should preferably be in contact with the alkali-treated fungi/glucan for a period long enough to ensure substantial neutralization throughout the composition. It will be appreciated that if the acidic agent is added first, then the alkaline agent should preferably be in contact with the acid-treated fungi/glucan for a period long enough to ensure substantial neutralization throughout the composition.

As noted above, during the reaction heat is generated. Thus the temperature can be monitored and the acidic agent and fungi/glucan can be left to react until the temperature starts to return to room temperature. This can be assessed manually with a thermometer or can be automated.

It may be that the acidic agent is mixed with the fungi/glucan during the full period of time they are in contact, or it may be that some of the contact time is at rest. For example, mixing may occur during from 10 to 100% of the contact time, e.g. from 50 to 100% or from 75% to 100% of the contact time. Thus mixing occurs during some, most or all of the contact time period.

Carrying out mixing allows the acidic agent to efficiently react with the fungi/glucan. The mixing is preferably even and steady.

The mixing of the acidic agent with the fungi/glucan may be carried out using any suitable mixing apparatus. The skilled person will appreciate that the viscosity of the composition should be taken into account in selecting a suitable apparatus. In one embodiment it is performed with a mechanical mixer, such as a planetary mixer or a pan type mixer or a conical screw mixer. It will be appreciated that the speed of mixing may be selected according to the scale of the process and the type of mixing apparatus. The mixing may, for example, be carried out at a speed in the range of from 10 to 1600 rpm. In one embodiment the mixing is carried out with a mechanical paddle at from 10 to 800 rpm, e.g. from 20 to 700 rpm, such as about 40 to 600 rpm. In another embodiment the mixing is carried out with a mechanical paddle at from 50 to 200 rpm, such as from 80 to 140 rpm, e.g. from 100 to 120 rpm. The present invention is not limited to a particular range of mixing speeds and these are purely exemplary. What is important is that, at the scale involved, the mixing speed is selected so as to produce an even, smooth blending of the product.

The mixing may suitably be carried out at around room temperature, e.g. from 15 to 25° C. For example, in one embodiment there is no external heat added. As noted above, the reaction is exothermic. The hotter the temperature of the preparation of the binder, typically the weaker the resulting products, e.g. boards, are. In one embodiment the binder is prepared at a temperature of from 10° C. to 80° C., such as from 15 to 60° C., but preferably from 15° C. to 45° C., such as from 15 to 40° C., and more preferably at around room temperature, e.g. from 15 to 25° C.

The mixing may suitably be carried out at around atmospheric pressure. For example, in one embodiment there is no external pressure applied.

As shown by the examples, it has been determined that the resulting pH of the binder does not significantly impact on the strength of the articles made therefrom. However, a binder of a certain pH can be preferable for other reasons, such as to prevent corrosion of the user's hands, the user's equipment and/or the filler material.

The pH of the binder can be selected to avoid damaging the filler material (e.g., wood) and to create a good cohesion with co-binding resins (e.g. crosslinkers) in the product.

In one embodiment, in the methods of producing a shaped article of the first and second aspects, in step a) the binder is produced in situ. Thus in step a) the binder is produced by mixing fungi/glucan and starch with an alkaline agent and an acidic agent. The quantities of alkaline agent and acidic agent may be selected such that the resulting binder after the acid and alkali treatments has a pH from 1 to 9, or 2 to 9 or 3 to 9, or 4 to 9; in one embodiment the pH may be from 5 to 9. The quantities of alkaline agent and acidic agent may be selected such that the resulting binder after the acid and alkali treatments has a pH from 1 to 8, or 2 to 8 or 3 to 8, or 4 to 8; in one embodiment the pH after the acid and alkali treatments may be from 5.5 to 8 or from 6 to 8. The alkaline agent and acidic agent may substantially or largely neutralize each other, or the alkaline agent and the acidic agent may produce an acidic binder.

As the skilled reader will appreciate, the pH of a material can be determined using a pH meter (a potentiometric pH meter, which measures the difference in electrical potential between a pH electrode and a reference electrode).

In some cases the pH of the resulting binder will change slightly after being left to stand. Therefore, the pH of the resulting binder is typically measured four hours (or more) after its manufacture.

In one embodiment the binder as used may have a pH of from 1 to 14, such as from 5 to 14, or from 5 to 12. In one embodiment the binder as used may have a pH of from 5 to 9, such as from 5.5 to 9, such as from 6 to 9, or from 7 to 9. For example, the binder as used may have a pH of from 5 to 8.5, such as from 5 to 8, or from 5 to 7.5, or from 5 to 7. It may be that the pH is from 5.5 to 8.5, such as from 5.5 to 8, or from 5.5 to 7.5, or from 5.5 to 7. In one embodiment the pH of the binder as used will be from 6 to 8, or from 6.5 to 8, such as about 7.

In one embodiment the binder as used may have a pH of from 3 to 7 or from 3 to 6.5. It may be preferable that the alkaline agent and acidic agent are added in quantities that produce a binder that is acidic, such as having a pH of from 3 to 6, to match the approximate pH of wood. It has been noted that binders with such pH values can be easier to mix with wood-based fillers than binders of more alkaline pH.

When considering the alkaline agent and acidic agent, the molar ratio of acid to alkali may be from 5:1 to 1:30, such as from 4:1 to 1:30, or 3:1 to 1:30, or 2:1 to 1:30; e.g. from 5:1 to 1:10, such as from 4:1 to 1:10, or 3:1 to 1:10, or 2:1 to 1:10. In one embodiment, it is from 1:1 to 1:30, such as from 1:1 to 1:20, or from 1:1 to 1:10, or from 1:1 to 1:8, or from 1:1 to 1:6. In one embodiment the molar ratio of acid to alkali may be selected such that the acid and alkali substantially neutralize each other. In one embodiment the molar ratio of acid to alkali is from 1:1.5 to 1.5:1, such as from 1:1.4 to 1.4:1, or from 1:1.3 to 1.3:1. In one embodiment, the molar ratio of acid to alkali is from 1:1.2 to 1.2:1, such as from 1:1.1 to 1.1:1. Thus it may be that the number of moles of acid is substantially equal to the number of moles of alkali.

The skilled person will understand that when calculating molar ratios, this must take into account the number of moles of acidic protons that are liberated from the acidic species and the number of moles of alkaline sites of the alkaline species, in accordance with the normal (N) unit. Therefore any such calculations must take into account whether the acid is monoprotic or diprotic, for example.

In one embodiment the alkaline agent is provided as an aqueous solution of an alkali which has a pKaH of 12 or more, e.g. 13 or more, and with the alkali concentration being 10% or more (e.g. 15% or more, such as from 15 to 50%, or 20% or more, such as from 20 to 45%) by weight of the alkaline agent, and wherein the acidic agent is provided as an aqueous solution of an acid which has a pKa of 1 or less, e.g. 0 or less, and with the acid concentration being 10% or more (e.g. 15% or more, such as from 15 to 50%, or 20% or more, such as from 20 to 45%) by weight of the acidic agent.

By carrying out this process of combining fungi/glucan with alkaline agent and acidic agent, a useful binder is obtained. Without being bound by theory, the strong binding ability of this binder is thought to be obtained due to re-linking (via covalent bonds and/or hydrogen bonds) of hydrolyzed material from the fungi cells/glucan, which occurs under broadly neutral conditions.

In one preferred embodiment the fungi is treated with alkaline agent and then with acidic agent. It has been found that treatment in this order of treatment helps the cells to be broken down and then be exposed to substantially neutral conditions, giving the most advantageously strong binding characteristics in the resulting binder. However, good strength characteristics are also seen when the fungi is treated with acidic agent and then with alkaline agent, as shown in the Examples, and depending on the intended end use these characteristics may be sufficient.

The shaped article comprises filler material dispersed through cured binder.

The binder according to the present invention may be prepared without any separation or extraction steps, such as filtration or centrifugation. This means that the production of the binder is simple, efficient and cost-effective. The binder as prepared can then be used directly, e.g. it may be directly combined with the filler material.

Therefore the binder can be prepared by a process that involves the combination of a number of materials but does not require any products to be removed. There are no unwanted by-products.

Furthermore, the binder as prepared has advantageous properties in terms of its viscosity. The binder as formed is a fluid paste with viscosity of less than 3000 centipoise.

The viscosity of a binder is important to allow for it to be easily mixed with filler material. In particular, the viscosity of a binder has to be sufficiently low so that it can be successfully mixed with filler material. A viscosity of less than 3000 centipoise allows the binder to easily mix with the filler material. In one embodiment, the viscosity of the binder of the present invention is from 100 to 3000 centipoise, such as from 100 to 2000 centipoise or from 100 to 1000 centipoise or from 100 to 750 centipoise. It may be that the viscosity is from 200 to 1000 centipoise, such as from 200 to 750 centipoise or from 200 to 700 centipoise. Preferably, the viscosity of the binder is less than 600 centipoise, such as from 200 to 600 centipoise, and most preferably from 200 to 500 centipoise.

For the binders of the present invention, a viscosity of 400-500 centipoise typically corresponds to a dry material content in the binder of 30-40% by weight. This ability to have a low viscosity with a relatively high content of dry material is a technical benefit of the present invention. Prior art binders normally require a lower dry material content (i.e. higher water content) to achieve a low viscosity.

Whilst the viscosity of a binder can be reduced by adding a diluent, such as water, doing so will typically lengthen the curing time of the binder due to the increased amount of water that will need to be removed during curing. Therefore it is a benefit of the present invention that the binder as formed after the acid and alkali treatment has a useful viscosity without needing further water to be added.

Viscosity can also be reduced by adding a cross-linking agent or a co-binding agent. It may be that from 1 to 40%, or from 2 to 40% of a cross-linking agent and/or a co-binding agent is added, such as from 2 to 30%, or from 3 to 20%, or more preferably from 5% to 15% by weight relative to the total weight of the binder.

The binders of the present invention are suitably non-toxic in the form when used. In particular, the binder of the present invention is substantially free of formaldehyde emissions, thereby meeting the safety, environmental and regulatory demands on the engineered wood industry.

The binder can be shaped and cured to form a strong three-dimensional shaped article. Such an article has excellent mechanical properties.

In the method of the first aspect, when a filler material is mixed with the binder in step b), the composition may be shaped into a three-dimensional shape, which is the desired shape of the shaped article, during or after the step of mixing the binder with the filler material.

In one such embodiment, moulding is used. It may be that a pre-mixed composition of binder and filler material is placed into a mould for shaping and then is allowed to cure, or it may be that the binder and filler material are mixed in the mould to form a shape and then this is allowed to cure.

The filler material is any material able to be dispersed in and bound by the binder. It is important to note that in the context of the present invention this broad definition of the term "filler material" is intended.

The filler material may comprise pieces that can be dispersed through the binder. The filler material may, for example, be particulate or granular or fibrous. It may in one embodiment be chopped, shredded or ground material.

The filler material is preferably sustainably sourced. It is preferably non-toxic. It may usefully be a natural material.

The filler material may comprise lignocellulose. In a preferred embodiment, the filler material comprises, or is, a wood-based filler, such as wood chips, saw dust, wood fibers and/or wood shavings.

A filler that includes lignocellulose, such as a wood-based filler material, is preferred, because it is believed that the cellulose in wood interacts with the binder and this improves the strength of the end product.

Preferably, the filler material is in the form of strands, fibers or chips. More preferably the filler material is in the form of strands, fibers or chips of wood.

It may be that the binder is mixed with the filler material to form a substantially homogenous blended composition. Therefore the filler material may be substantially evenly distributed throughout the binder before curing. In an alternative embodiment, the filler may be distributed non-evenly, for example there may be a denser concentration of filler at the top or at the bottom or in the middle, or the filler may comprise different size pieces and the larger size pieces may be concentrated at one location, e.g. towards the middle.

In general, in the invention one or more additives may optionally be added to the binder before curing. In one embodiment these are added during step b). In a preferred embodiment a cross-linker is added immediately before or during step b). The binder preferably comprises a crosslinking agent, such as polyamidoamine epichlorohydrin, in an amount of up to 40% by weight.

The binder can usefully be combined with filler material before or during curing. The filler may be any material that can be dispersed in and bound by the binder. The binder has been found to be excellent at binding filler materials, in particular wood-based filler materials, to form cured three-dimensional articles having the filler material dispersed throughout.

In the method of the first aspect, the shaping is carried out by use of a mould, e.g. by press moulding. Therefore, for example, the shaping may comprise shaping the composition into a panel, sheet or tile shape.

The articles of the present invention may be resilient and strong, for example, in terms of their resistance to forces such as compression or in terms of its durability.

As will be described further in the Examples section, the binders have been found to contain no formaldehyde. Therefore, these binders can be employed as formaldehyde-free alternatives to urea-formaldehyde resins used in the engineered wood industry. Thus these binders can be used to bind together wood-based filler material to form shaped articles which are composite wood products, such as particle boards, plywood and medium-density fiberboards (MDFs).

In addition, by using filler material that is from sustainable sources, the article of the invention is obtainable from sustainable sources. The filler material may usefully be chosen as a natural material, but synthetic materials may also be contemplated.

Thus the present invention permits the production of a strong and resilient article that can be utilized for construction, packaging and the like, but which is a "green" product in the sense that it is non-toxic and it uses natural and sustainable raw materials.

The binder of the invention may be used in combination with known binders, as co-resins. When the binder is used in combination with a co-resin, the co-resin may be used in an amount of up to 60% by weight of the combined binder plus co-resin, e.g. from 0.5 to 50% or from 1 to 40% or from 5 to 30%. It may be that the co-resin is selected from the group consisting of urea-formaldehyde, melamine-formaldehyde, and pMDI.

Due to the fact that the present binders have excellent properties, especially in terms of strength, the amount of known binder, e, g. urea formaldehyde, can be reduced as compared to what is conventional. Therefore even when used in combination with less environmentally friendly binders, the net effect is a reduction in negatives, e.g. a reduction in the amount of formaldehyde emitted. In one embodiment the binder of the invention is used in combination with one or more co-resins, e.g. urea formaldehyde, in a weight ratio of from 100:1 to 1:2, such as from 50:1 to 1:1, e.g. from 50:1 to 2:1.

The articles of the present invention may be durable for a period of six months or more, such as five years, before degrading. The article may have a longer durability indoors than outdoors.

The articles of the present invention may, in one embodiment, find use as non-toxic, sustainably sourced alternatives to engineered wood panels. In particular, it is envisaged that the articles may be suitable replacements for conventional fiberboards (such as high-density, medium-density or low-density fiberboards), insulation boards, particle boards, oriented strand board (OSB) or plywood. Thus the articles may, in one embodiment, be in the form of panels, sheets or tiles.

In one embodiment, the article may be a temporary or permanent construction material, such as flooring, roofing or wall paneling.

The article may, for example, be shaped in the form of a flooring tile. The flooring tile my have any shape but in one embodiment they may be square or rectangular or hexagonal. These tiles may be formed into an array, which may be substantially planar. In one embodiment the tiles are temporarily or permanently linked together in the array form to provide a flooring structure. This flooring structure may be laid down for outdoor events, such as festivals or markets or weddings. This flooring structure can therefore serve to protect the underlying land and/or to provide a flat and even surface and/or to provide a clean and dry surface.

The article may also be used in the packaging industry. In this regard, the article may be shaped in the form of a crate, box or tray. For example, the article may be a moulded tray which can be used to hold food-stock, such as fruit or vegetables, e.g. during transportation and/or display. The present invention is especially beneficial in this application due to the article being non-toxic and being formed from cheap, readily available and sustainable raw materials.

One or more filler material is combined with the binder to form a composition that is cured to obtain the article according to the invention. The binder may be combined with a filler material by hand or using a blending machine, such as a planetary mixer, a rotating drum mixer, or a roller (particularly when viscosity is high, and for surface applications). The binder may be sprayed onto the filler material, which will improve the spreading over the filler material, and which is particularly suitable if the binder is of a low viscosity, such as 500 cP or less, preferably 300 cP or less, such as from 300 cP to 100 cP.

When filler material is combined with the binder, it will be understood that the amount of binder will depend on the nature of the filler material and both the intended use and desired properties of the article. For particle boards or fiberboards, the binder will typically make up from 5 to 15% of the composition by weight on a dry weight basis. For plywood, the binder will typically be used in an amount of from 100 to 300 g/m$^2$, such as from 140 to 250 g/m$^2$ for each surface that the binder is applied to. In one embodiment, the binder makes up 1% or more of the composition or 5% or more of the composition or 10% or more of the composition, e.g. from 5 to 90% by weight of the composition, for example from 10% to 80% or from 10 to 75% by weight of the composition. In one embodiment, the binder makes up from 10 to 60% by weight of the composition, or from 1 to 50% or from 15 to 50% by weight of the composition, e.g. from 20 to 50% by weight of the composition. For cold curing applications, the amount of binder will usually be higher, such as from 30 to 70% of the composition by weight or from 40 to 60% of the composition by weight. In one embodiment the amount of binder is up to 50% of the composition by weight.

Suitable fillers may include one or more natural materials, e.g. selected from wood-based filler (e.g. wood chips, wood fibers, wood shavings, saw dust or the like), fly ash, mineral solid residue such as egg shells (e.g. powdered egg shells), crustacean shell (e.g. powdered crustacean shell), algae (e.g. microalgae, powdered algae residue), feathers, flour (e.g. rice flour or wheat flour), hemp, bonemeal, plastics (such as bio-based plastics and bio-degradable plastics), granulate fertilizer, quartz, glass fibers and flax fiber and combinations thereof. Preferably the filler will include wood-based filler (e.g. wood chips, wood fibers, wood shavings, saw dust or the like). However, it will be appreciated that the binder can bind any solid material in particulate, granular or fibrous form, and thus the filler material is not specifically limited. The filler material may be organic or inorganic in origin.

In one embodiment, the filler material comprises wood-based filler, e.g. wood chips, wood shavings and/or saw dust. As noted above, this allows a product to be provided which is a non-toxic, sustainably sourced alternative to currently available engineered wood panels.

It will be understood that the type of filler material will somewhat depend on the desired type of engineered wood product of the article. For example, wood chips are used for particle boards; wood fibers are employed for medium- and high-density fiberboards; strands are used for oriented strand board; veneers or plies are used for plywood; and timber is used in cross-laminated timber and glued laminated timber (glulam). Sawdust is used in several products to smooth surfaces.

Filler material may be mixed with the binder in any suitable amount. In one embodiment, in the composition as formed in step b) the filler material makes up 5% by weight or more of the composition, such as 10% or more.

It may be that the filler material makes up from 10% to 99%, such as from 15 to 95%, or from 40 to 95%, or from 70 to 95%, or from 70 to 90%, by weight of the composition. In one embodiment, the filler material makes up from 10 to 90% by weight of the composition, for example from 15% to 85% or from 20 to 80% by weight of the composition. In one embodiment, the filler material makes up from 25 to 90% by weight of the composition, such as from 40 to 85% or from 50 to 80% by weight of the composition. These amounts are by weight of the composition, when considered on a wet weight basis.

A range of different ratios of binder to filler can be contemplated and the invention is not limited to any particular ratios. In one embodiment, the ratio of binder to filler is from 1:1 to 1:100, such as from 1:2 to 1:50 or from 1:4 to 1:20, or 5:1 to 1:10, such as from 3:1 to 1:8, e.g. from 2:1 to 1:6 or from 1.5:1 to 1:5 or from 1:1 to 1:4.

In one embodiment, in the composition as formed in step b) the binder makes up from 2 to 90% by weight of the composition, such as from 2 to 70%, or from 2 to 50%, or from 2 to 30%, or from 2 to 25%. It may be that the binder makes up from 5 to 90% by weight of the composition, such as from 5 to 70%, or from 5 to 50%, or from 5 to 30%, or from 5 to 25%. These amounts are by weight of the composition, when considered on a wet weight basis. These amounts do not include any optional additives that may be added to the binder before the shaping and curing steps, such as crosslinkers.

A benefit of the present invention is that relatively large quantities of filler material can be held together in the form of a strong shaped 3D article by a relatively small amount of binder.

It may be that the total of binder plus filler material in the composition to be cured is 70% or more of the total composition by weight, e.g. 75% or more, or 80% or more, or 85% or more. In one embodiment the total of binder plus filler material in the composition to be cured is from 75 to 95% by weight, e.g. from 80 to 95% by weight. In one embodiment the total of binder plus filler material in the composition to be cured is from 75 to 100% by weight, e.g. from 80 to 100% by weight.

In one embodiment, one or more additives may optionally be further included in the composition. Suitable additives include, but are not limited to, biological agents, thickening agents (where this agent is not the starch that is an essential component of the invention), hydrophobic agents, curing agents, crosslinking agents, and/or wetting agents. Preferably the composition includes a crosslinking agent.

In one embodiment, the invention uses binder, filler material and one or more additives in the composition that is shaped and cured.

Additives that are included may be added at any suitable stage. They may be provided pre-combined with the binder or may be mixed with the binder. They can be added before, during or after mixing of binder plus filler material. They may be provided pre-combined with the filler material or may be mixed with the filler material.

Generally, when present, additives may be included in a total amount of up to 25% by weight of the composition, e.g. up to 20%. For example, additives may be included in a total amount of from 1 to 20%, such as from 2 to 15% or from 5 to 10%, by weight of the composition.

Starch is required as an essential component of the invention. The skilled person will appreciate that starch is a thickening agent. In one embodiment, additional thickening agents which are not starch may be included as additives. As the skilled person will appreciate, thickening agents increase the viscosity of a substance. Such increased viscosity that comes from the use of these agents may be undesirable because it can make a binder more difficult to mix with filler material. They can also increase the gelation time of a mixture.

Curing agents may be included as additives. In particular, crosslinking agents may be included as additives. As the skilled person will appreciate, crosslinking agents can increase the structural stability of a material.

Crosslinking agents that can be contemplated for use include amino crosslinkers, phenolic cross linkers, and isocyanates/polyurethanes.

Specific examples of crosslinking agents that can be used include polyamidoamine epichlorohydrin (PAE) resin, palmitoil chloride and epoxy resins. Preferably, PAE resin is used as a crosslinking agent. Hercosett 617 is an example of a PAE resin. This is distributed as a liquid resin with about 13% solid content and is available from Solenis.

In particular, the binder preferably comprises a crosslinking agent, such as polyamidoamine epichlorohydrin, in an amount of up to 40% by weight, or up to 20% by weight, or 1% to 40% by weight, such as 2% to 30% by weight, or 5% to 20% by weight; preferably from 5 to 12% by weight.

Co-binding agents may be included as additives. As the skilled person will appreciate, co-binding agents may have properties that complement the binder according to the present invention. For example, formaldehyde-based resin, such as urea-formaldehyde, melanine formaldehyde and/or phenol formaldehyde, may be included as co-binding agents. Despite these co-binding agents comprising formaldehyde, the skilled person will be aware that the use of the binder of the present invention allows a smaller amount of formaldehyde-based co-binding agent to be used, therefore still reducing the amount of formaldehyde in an engineered wood product. In one embodiment, a co-binding agent is an isocyanate resin, such as polymethylene diphenyl diisocyanate (PMDI), polyhexamethylene diisocyanate (PHDI), toluene diisocyanate, and/or polyurethane. For example, the binder may comprise an co-binding agent in an amount of up to 70%, such as up to 60%, or up to 50%, or up to 30%, for example up to 20% by weight. In one embodiment, the binder comprises a co-binding agent in an amount of from 1 to 60%, or from 1 to 50%, such as from 5 to 30%, or from 10 to 20% by weight, or from 40% to 60% by weight.

Additives, such as crosslinking agents and co-binding agents may, at least initially, decrease the viscosity of the binder, thereby allowing the binder to be more easily mixed with the filler. Using an additive such as a crosslinking agent or a co-binding agent to reduce the viscosity of the binder is preferable to using water to perform this task as the addition of further water will increase the pressing and curing time that an engineered wood product will require. Even the addition of a small amount of additive, such as up to 10% of additive by weight, or 5-10% of additive by weight may have a significant impact on the viscosity of the binder. Preferably, the addition of additives, such as 5-10 wt % of PAE, decreases the viscosity of the binder to 500 cP or less, to allow the binder to flow from the reaction vessel.

The skilled person will appreciate that the additive may have a water content and therefore will contribute to the total water content of the binder product. In some embodiments the water content of the additive is up to 95 wt %. Clearly the impact on the water content of the binder product will depend on both the water content of the additive and the amount of additive added.

In one embodiment, a cellulose derivative such as carboxymethyl cellulose (CMC) is added to the binder. Cellulose derivatives such as CMC bind well to polyamidoamine epichlorohydrin resins, such as Hercosett 617. Therefore, cellulose derivatives such as CMC may be added to the filler material, in particular a wood-based filler material, to increase tack and further enhance strength. The binder may comprise a cellulose derivative, such as carboxymethyl cellulose, in an amount of 1% to 40% by weight, such as 2% to 30% by weight, or 5% to 20% by weight.

Minerals may be included as additives. In particular, silicates, such as phyllosilicates, e.g. bentonite and/or montmorillonite, and/or silica nanoparticles can strengthen the binder. Such minerals may be used in amounts of up to 10% of the binder by weight, such as in amounts of 0.5% to 6% of the binder by weight.

Fungicides and/or biocides may be included as additives. Such agents can be employed directly in the wood to delay or prevent the colonization of the wood by bacteria and fungi. Suitable fungicides/biocides include borates, essential oils (such as from coconut and/or palm oils), tannins and chitosan. Fungicides/biocides may be used in amounts of from 0.1 to 5% by weight, such as from 0.5 to 5% by weight, or from 0.5% to 3% by weight, or from 0.5% to 1% by weight. The binder could be applied to the article or added to the binder, for example.

Hydrophobic agents may be included as additives. As the skilled person will appreciate, hydrophobic agents are resistant to water. Thus they can protect a substance from absorbing moisture from the air and potentially disintegrating due to being dissolved by water. However, hydrophobic agents may reduce the adhesive properties of the binder and should be used sparingly. Such agents are, therefore, useful for maintaining stability over a range of humidity conditions. Examples of hydrophobic agents include waxes, such as naphtha wax and natural bee wax, and palm oil compounds. In one embodiment a hydrophobic agent is added to the binder in an amount of up to 0.5% by weight relative to the weight of the filler material. In one embodiment, the filler material is directly treated with a hydrophobic agent, either before or after treatment with the binder, in an amount of up to 0.5% by weight relative to the weight of the filler material.

Curing agents may be included as additives. As the skilled person will appreciate, curing agents help the curing process. This can be by initiating it or facilitating it, especially in the presence of heat. Examples of curing agents include compounds in the amidoamine family.

Wetting agents may be included as additives. As the skilled person will appreciate, wetting agents lower the surface tension of liquids, allowing the liquids to more easily spread across the surface of an article. Substances with anti-caking properties typically allow for better wetting. Examples of wetting agents include palm oil or palm oil compounds (e.g. palmitoil chloride or other compounds comprising palmitoil chloride), coconut oil and glycerol monostearate.

The moisture content of the binder is preferably controlled to avoid blistering and excessive steaming in the hot pressing phase, which may not only increase the time required for pressing but also disrupt existing bonds. The dry weight of the binder should be from 25% to 65% by weight of the binder, such as from 30% to 60%. In a preferred embodiment, the dry weight of the binder is from 35% to 55%, or from 35% to 50%, such as from 35% to 45%. The optimal dry weight of the binder is about 40%.

The moisture content of the binder may be reduced by additional drying steps, which is preferably performed in a batch-wise manner. This may be performed by air-drying, where natural convection and airflow carries away water, which is slow but cheap and can be done in a tray, pan or rotary drier (e.g. a drum shaped rotary drier). Hot air may be employed to accelerate the speed at which the moisture content of the binder is reduced, which avoids pre-curing. For example, the hot air may be applied at a temperature of from 30 to 100° C., such as from 40° C. to 90° C. Moisture can be added by mixing the binder with water.

The method of the present invention may optionally include a treatment for the binder with a bleaching agent, such as sodium hypochlorite, hydrogen peroxide, or ozone. This step may decrease the odour and/or lighten the colour of the binder. By-products of this treatment may be removed during an additional drying step, if necessary.

The method of the present invention may optionally include a treatment for the binder, prior to mixing the binder with the filler material. For example, this may be a pre-heating treatment. In one embodiment the binder is heated to a temperature of 30 to 60° C., such as from 30 to 50° C. or from 30 to 40° C. This can assist in making the binder less vicious before mixing with the filler material. It can also assist if the product is made by hot pressing, because the binder composition is then above room temperature already when it is hot pressed.

In general, the binder may be at a temperature of from 15 to 60° C. when it is mixed with the filler material, e.g. from 20 to 50° C.

The method of the present invention may optionally include a treatment for the filler material, prior to mixing the binder with the filler material. For example, this may be to wash, dry and/or bleach the filler material, and/or it may be that the filler material is chopped or ground into smaller particles. This may achieve a particularly desirable appearance and/or mechanical or chemical characteristics for the resulting article.

In the method of producing an article, the composition which comprises the binder, filler material, and any optional additives, is shaped and cured.

Thus the composition is shaped into a three-dimensional shape, which is the desired shape of the shaped article, before or during curing. In one embodiment, the shaping is carried out by use of a mould (e.g. by press moulding), by 3D printing, by casting, by pressing or by sculpting. In one embodiment, the composition is rolled into shape by rollers. In another embodiment, the composition is compressed into shape under pressure.

The pressure applied during the shaping and/or curing may, in one embodiment, may be 0.5 MPa or higher, e.g. from 0.5 to 7 MPa, such as from 0.5 to 6 MPa or from 0.5 to 5 MPa and especially between 0.5 and 4 MPa. For particle boards, it will usually be 1 Mpa or higher, such as from 1 to 5 MPa, e.g. from 1 to 4 MPa, and for MDF it will usually be 1 MPa or higher, such as from 1 to 5 MPa, e.g. from 1 to 4 MPa. For plywood, the pressure will usually be from 0.5 to 1.5 MPa.

Heat may be applied during the shaping step, e.g. up to 80° C., or the shaping may be carried out at room temperature.

Heat may be applied during the curing step, e.g. a temperature of from 30 to 250° C. may be used, such as from 30 to 70° C.; preferably the curing temperature is from 50 to 250 or from 75 to 250° C.; such as from 100° C. to 230° C., and preferably from 150° C. to 210° C. Alternatively cold curing may be used, i.e. room temperature (15 to 25° C.). In one embodiment the temperature during curing is from 15 to 250° C., e.g. from 15 to 230° C., such as from 20 to 210° C.

Before or after shaping, the composition may be stacked and/or layered with other compositions so as to form a composite product once shaped and cured.

When a filler material is included, the composition may be shaped into a three-dimensional shape, which is the desired shape of the shaped article, during or after the step of mixing the binder with the filler material.

In one preferred embodiment a mould is used for shaping. A release agent may be applied to the mould before the binder composition is placed in the mould, to aid removal of the cured article. Thus the composition is placed in the mould before curing, such that the article takes on the shape of the mould when it cures. In one embodiment the composition is pressed into a mould.

The cured article can then be removed from the mould post-curing. This is conventional and known in the art. Thus a stand-alone, shaped article is provided.

The composition may be cured at room temperature and atmospheric pressure ("air drying). In this case, complete curing will normally occur over a period of 7-14 days, depending on humidity.

The composition may be cured at elevated temperature and/or pressure. This leads to reduced time periods for curing to be completed.

In one embodiment, curing may be aided in a drying device, where the temperature is increased above room temperature and air is allowed to flow. The pressure can be atmospheric pressure. An industrial oven may be used for this purpose. In one such embodiment the temperature is in a range of from 30 to 70° C. In this case, complete curing will normally occur over a period of 30 minutes to 24 hours, e.g. 1 to 12 hours, depending on temperature and humidity.

In a preferred embodiment, curing may be aided with the application of pressure as well as elevated temperature, for example with a hydraulic heat press ("hot-press") device. Such devices typically apply from 1.4 to 4 MPa, such as from 1.4 to 3.5 MPa, e.g. from about 2 to 3 MPa, of pressure for from 1 to 15 minutes, e.g. from 3 to 10 minutes or from 3 to 5 minutes, at a temperature in a range of from 100° C. to 300° C., such as from 100° C. to 200° C., or from 100° C. to 230° C., or from 175° C. to 225° C., or from 120° C. to 180° C. Preferably a temperature in a range of from 150° C. to 250° C. or from 150° C. to 210° C. is used. Preferably a temperature in a range of from 150° C. to 250° C. is used for from 3 to 10 minutes. The temperature used in the curing process may depend on the desired type of engineered wood product. For example, plywood may be cured at a temperature of from 80° C. to 120° C.; fiberboards, such as medium-density fiberboard, may be cured at a temperature of from 170° C. to 210° C.; and particleboards may be cured at a temperature of from 160° C. to 210° C.

In general, curing the binder fully requires raising the core temperature to about 104° C. or higher.

The pressure applied to the article by the press may be an important factor. Excessive pressure can cause the disruption of bonds within an article, whilst insufficient pressure can produce an article that is not strong or dense enough. The pressure applied by a press, such as a hydraulic heat press, may be up to 13.8 MPa, such as 0.48 to 6.9 MPa. The pressure used in the curing process may depend on the desired type of engineered wood product. For example, particleboard may be cured at 1.38 to 3.5 MPa; fiberboards, such as medium-density fiberboard, may be cured at 0.48 to 5.2 MPa; and plywood may be cured at 0.68 to\2.1 MPa. In particular, the low pressures used for plywood prevent the veneers from warping.

It may be that curing the binder within a hydraulic heat press partially cures the binder and the article provided therefrom may benefit from resting in atmospheric conditions for a period of up to two weeks to allow the article to cool and to allow the binder to completely cure. In one embodiment, following the curing step, the article is rested in atmospheric conditions for a period of up to two weeks, such as three days to two weeks.

As the exposure to high temperatures is only for a short period in this curing technique this is acceptable and does not adversely affect the desired properties of the articles.

In another embodiment, curing may be aided with the application of pressure but at room temperature. For example, the composition may be compressed into a mould using a hand press before being left to cure under atmospheric conditions. A hand press may have a capacity of from 0.5 to 12 kN, e.g. from 0.75 to 7.5 kN or from 1 to 5 kN. Pressure may suitably be applied for from 1 to 10 minutes before being left to cure under atmospheric conditions.

In some embodiments of the invention, the binder is used as an adhesive to secure two component parts together, to produce a composite product. The binder is therefore applied to a contact surface of one or both component parts before bringing them together.

The contact surfaces may be made of any suitable material. Examples include wood (including engineered wood products, such as chipboard), glass, paper, cardboard and plastic. The contact surfaces may be the same or different.

The binder may be applied to a contact surface of a component part by any suitable means. For example, the binder may be spread on the contact surface using an applicator. The skilled person will be aware of glue applicators, e.g. of the type that apply glue to a surface by use of spray nozzles that spray the glue over the roll. Alternatively, it may be applied without spreading, e.g. it may be deposited onto the contact surface from a nozzle or other supply means. It will be understood that the act of bringing the contact surfaces together may spread the binder.

In one embodiment, once the contact surfaces are brought together pressure is applied. This can assist with securing the surfaces together.

The binder may be applied to only one of the two contact surfaces before the two contact surfaces are brought together. Alternatively, the binder may be applied to both contact surfaces before the contact surfaces are brought together.

The binder may optionally be allowed to partially cure, as with contact adhesives, prior to the surfaces being brought together.

The time for curing of the binder to secure the two contact surfaces together may depend on factors such as the material(s) that the component parts are formed from, the size of the contact surfaces, the temperature of curing and the humidity. As such, curing may take place at room temperature over a period of time of up to 7 days. It may be from 10 minutes up to 72 hours, e.g. from 30 minutes up to 48 hours, or from 1 to 24 hours. Curing to secure the two contact surfaces together may be accelerated at higher temperatures, for example at from 30 to 70° C., and/or with application of pressure. Under such conditions, curing may occur over a period of time of up to 24 hours, e.g. from 1 minute up to 6 hours, or from 2 minutes up to 3 hours, or from 5 minutes up to 1 hour, depending on the temperature chosen.

The binders of the present invention may find many useful applications as adhesives. For example, the binders of the present invention may be used as adhesives in construction or furniture applications, e.g. to create laminate sheet products or to join together component parts of a furniture article, or in the packaging industry, such as for adhering labels to glass bottles or jars.

The articles of the present invention may be, for example, construction articles, such as insulation boards (such as low-density insulation boards); flooring structures or roofing structures (including tiles, sheets and panels); packaging articles, such as crates, boxes or trays; or furniture articles, such as tables, chairs or stools. However, the invention is not limited to a particular type of article.

The articles of the present invention may be used, for example, as replacements for plastic articles and for traditional engineered wood articles, such as formaldehyde-urea resin-bound articles, e.g. particle board panels. Engineered wood panels are normally square or rectangular shaped and can commonly have a depth (thickness) of 2 mm or more, especially 5 mm or more or 9 mm or more or 10 mm or more, e.g. around 2 to 50 mm, such as 15 to 40 mm, e.g. 12 mm or 18 mm or 22 mm or 30 mm or 38 mm. Particle board panels will normally be square or rectangular shaped and can commonly have a depth of 5 mm or more, especially 8 mm or more or 9 mm or more or 10 mm or more, e.g. around 10 to 50 mm, such as 15 to 40 mm, e.g. 12 mm or 18 mm or 22 mm or 30 mm or 38 mm. Fiberboard panels, such as MDF panels, are normally available with a depth of 3 mm, 6 mm, 9 mm, 12 mm, 15 mm, 18 mm or 25 mm.

The article may be in the form of a regular shape, e.g. a rectangular, square or hexagonal panel or sheet or tile. The shaped articles can be standard shapes, such as square or rectangular sheets or panels, but the invention is not limited to particular shapes.

The invention will now be further described, in a non-limiting manner, with reference to the following examples:

EXAMPLES

In the following examples, unless stated otherwise a yeast-based binder (*Saccharomyces cerevisiae*) was obtained and used. However, it will be appreciated from the above discussions that other fungi may be used to form the binder.

Examples 1 to 7 present a first embodiment of a binder according to the invention (binder A), and illustrate its properties and versatility through various prototypes.

Examples 8 to 12 describe a second embodiment of a binder according to the invention (binder B) that has been adapted for application in the engineered wood industry, and more specifically, for particleboards and MDF, and its performance is assessed from lab-scale tests and larger scale industry standard tests.

Example 1: Synthesis of Yeast-Based Binder A

NaOH (as a 30 w/w % aqueous solution) and dry powdered baker's yeast (8 wt % moisture content) were mixed in a mechanical mixer at 6000 rpm for about 10-15 minutes to form an alkaline composition, which is a sticky brown paste. After this period of time vapour emissions decreased.

HCl (as a 30 w/w % aqueous solution) was then added to the paste and mixed using the mechanical mixer at 6000 rpm for about 10-15 minutes.

The resulting binder was homogeneous in appearance.

Different amounts of the three reagents were used to form a range of binders, each having a resulting pH in the range of 5.6 to 8.

The best results were obtained when the reagents were used in approximately equal amounts (respective ratios of in the range of 1.5:1 to 1:1.5 for each and every pair of the reagents, especially in the range of 1.2:1 to 1:1.2). Thus acidic agent: alkaline agent is preferably in the range of 1.2:1 to 1:1.2; acidic agent: fungi is preferably in the range of 1.2:1 to 1:1.2; and alkaline agent: fungi is preferably in the range of 1.2:1 to 1:1.2.

In particular, the following may be used:
NaOH: 360 g, as a 30 w/w % aqueous solution
dry powdered baker's yeast: 360 g, 8 wt % moisture content.
HCl: 360 g, as a 30 w/w % aqueous solution The resulting binder had a pH of about 7 and was homogenous in appearance.

Example 2: Production of Tiles Using Yeast-Based Binder A

Compositions were formed from the binder produced in Example 1, filler material, plus one or more additives. The binder and filler material were used in a 1:1 ratio and making up at least 80 wt % of the total composition.

Exemplary composition:
Binder as formed in Example 1: 45% w/w
Palm oil (crosslinking agent): 1% w/w
Coconut oil (crosslinking agent): 1% w/w
Naphtha wax (hydrophobic agent) 1% w/w
Dextrin (thickening agent) 7% w/w
Filler material: 45% w/w.

A number of different articles were produced using different filler materials:
a) Wood chips
b) Microalgae powder
c) Mixed saw dust, fly-ash and egg shell powder
d) Mixed fly-ash and ground chicken feathers In each case the resulting composition was placed into a mould.

In this regard, the composition was compressed into the mould using a 200 kg-force hand press before being left to cure for 10 days under atmospheric conditions.

The article formed according to this method was a tile measuring approximately 1 cm in depth by 10 cm diameter.

The tiles as obtained are shown in FIGS. 1a) to d).

As can be seen, the tiles as produced had a complex (irregular) shape. Further, the mould had allowed the product to form with surface definition showing a logo. However, regular shaped tiles, e.g. square or hexagonal tiles, can also be produced in the same manner.

Example 3: Toxicity Testing of Tiles

A microalgae-based tile as formed above was tested for conformance with European standard EN 71-3, showing that the level of migration of certain elements from the product (as determined by using ICP-OES spectrometry) is low enough that it could be used in toys.

All Results and Limits are Quoted mg/kg of Named Material.

TABLE 1

| Element | Al | Sb | As | Ba | B | Cd | Cr | Co | Cu | Pb | Mn | Hg | Ni | Se | Sr | Sn | Zn |
|---|---|---|---|---|---|---|---|---|---|---|---|---|---|---|---|---|---|
| EN71-3 Limit | 70000 | 560 | 47 | 18750 | 15000 | 17 | NA | 130 | 7700 | 160 | 15000 | 94 | 930 | 460 | 56000 | 180000 | 46000 |
| 1 | 150 | <10 | <10 | <10 | 38 | <1.0 | 0.27 | <10 | <10 | <10 | 11 | <10 | <10 | <10 | 12 | <10 | 41 |

The tile was also tested for the amount of free formaldehyde and formaldehyde extracted partly through hydrolysis by means of a water extraction, in accordance with BS EN ISO 14184-1:2011. This procedure measures free and hydrolysed formaldehyde in quantities between 16 mg/kg and 3500 mg/kg.

The tests detected no formaldehyde, i.e., the level of formaldehyde was below 16 mg/kg.

The tile is therefore beneficial in terms of being formaldehyde free. It is a non-toxic alternative to current products.

Example 4: Strength Testing for Tiles

A microalgae-based tile as formed above was subjected to compression tests. The tile withstood a 9.5 kN force without any signs of disintegration.

Further, each of the tiles as shown in FIGS. 1a) to d) were able to be dropped from a 1 meter height onto a hard floor without breaking, chipping or cracking.

Example 5: Production of Sheets and Panels Using Yeast-Based Binder

Compositions were formed from binder, filler material, plus one or more additives. For panels, the binder and filler material were used in a 20:80 ratio and making up at least 80 wt % of the total composition.

Exemplary Composition:
Binder as formed above: 18% w/w
Palm oil (crosslinking agent): 1% w/w
Coconut oil (crosslinking agent): 1% w/w
Naphtha wax (hydrophobic agent) 1% w/w
Dextrin (thickening agent) 7% w/w
Filler material: 72% w/w.

The filler materials used were:
i) a 50:50 blend of microalgae powder and natural fibres (ground chicken feathers)
ii) wood chips.

The resulting composition was pressed into the form of (i) a sheet and (ii) a panel before being cured.

In particular, the filler material and binder and additives are placed into a mould, to form a mat. The mould consisted of a bottom tray, a top tray and a shaped guide. The shaped guide was square but rectangular or other shapes could of course also be used. The trays used were metal.

In the case of ii) there were wood chips of different sizes used in layers, with a layer of larger size chips being used towards the middle and layers of finer sized chips being used towards the top and bottom surfaces. A former may be used to achieve even stratification, or hand tools may be used to shape the layers.

Rollers were used to apply pressure to flatten the upper surface of the mat.

In the case of ii) the mat was then pre-pressed at room temperature. This can be done by hand or using a cold press. This step is optional but reduces the size of the chip mass, ensures greater contact between the chips and reduces the time the product has to spend in the hot press in the subsequent main cure step. The pressures used in the pre-press step are lower than those in the main cure step.

The shaped guide surrounding the mat can then be removed at this stage. For example, the trays and mat can be raised up together, leaving the shaped guide behind. The mat retains the shape of the guide and rests on the bottom tray.

A hot press is used to cure the shaped mat. This is carried out at elevated temperature, of 150 to 200° C., and with a pressure applied of 20-35 kg cm$^{-2}$ for 3 to 10 minutes.

The cured product is then ready.

The articles formed according to this method were:
i) a microalgae sheet, measuring approximately 1 mm in depth;
ii) a particle board panel, measuring over 5 mm in depth.

Figure 1E:
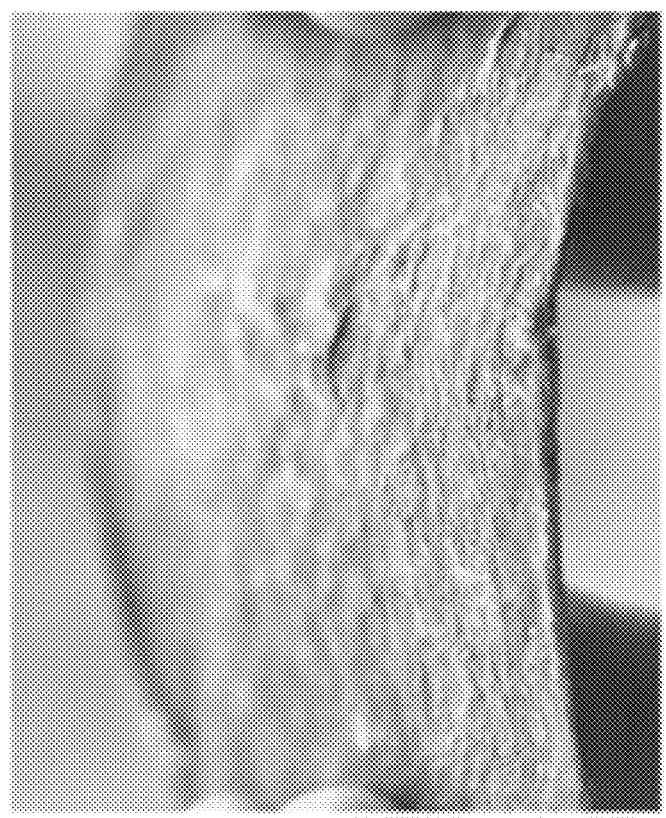
FIG. 1e depicts an algae-based sheet panel in accordance with this disclosure.

The sheet and panel as obtained are shown in FIGS. 1e) and 1f) respectively.

As can be seen in FIG. 1e), the algae-based sheet panel as produced is resilient—it is shown being bent. When bent it did not crack, chip or break.

The particle board panel as in FIG. 10 is strong and can be used as a non-toxic alternative to current formaldehyde resin-based composite wood products.

Example 6: Use of the Binder as an Adhesive 3 grams of binder as formed above was used to glue two 5 cm×5 cm blocks of wood together. The binder was applied to the top planar 5 cm×5 cm surface of one block, before being brought into aligned contact with the bottom planar 5 cm×5 cm surface of the other block.

Pressure was applied by hand and the binder was allowed to cure at room temperature for 10 minutes to secure the two blocks together, to provide a composite product.

Example 7: Strength Testing on Composite Products

A composite product, formed as above, was subjected to forces to determine the adhesive strength of the cured binder. One wooden block of the composite product was held securely whilst the other block was subjected pulling forces applied from the centre of the block, in a direction perpendicular to the glued surface. The pulling forces were applied using weights.

The weights were increased until the blocks came apart.

The composite product withstood a pulling force from a load of up to 45 Newtons before the wooden blocks came apart.

A comparative composite product, formed by the above method but using PVA wood glue in place of the binder, was found to come apart following application of a load of only 23 Newtons.

Therefore, the binder of the product of the invention is a superior adhesive as compared to conventional adhesives.

Example 8: Synthesis of Yeast-Based Binder B

Baker's yeast (250 g, ~5% water content, sold under the brand Fermipan, sourced from Lallemand) and dextrin (13 g, ~1-5% water content, sourced from Atlantis Art Materials) were mixed dry. Any lumps (agglomerations) of yeast or dextrin were crushed.

Water (320 ml) was then added to the yeast and dextrin mixture to assist mixing, because the yeast material had a very low water content. The yeast, dextrin and water were mixed in an orbiter (Morphy Richards Standing Orbiter 400020) at 100 to 123 rpm (Speed 6 on the machine). It was ensured that any lumps of material were broken up and that the mixture was homogenous. The resulting mixture had a pH of about 7.

Sodium hydroxide (32 g, 37 wt % solution in water) was added to the orbiter and mixed at 100 to 123 rpm for 1-2 minutes to form an alkaline composition. It was again ensured that any lumps of material were broken and that the mixture was homogenous. The resulting mixture had a pH of about 11-12.

HCl (52 g, 14 wt % solution in water) was then added to the alkaline composition. The mixture was mixed in the orbiter at 100 to 123 rpm (Speed 6 on the machine) for 6 minutes to afford yeast-based binder B (667 g) as a light brown, creamy substance with a molasses-like viscosity.

Yeast-based binder B had a dry content of 40%. Yeast-based binder B initially had a pH of about 9, which fell to around 6-7 after being left to stand for four hours.

Example 9: Production of Boards and Panels Using Yeast-Based Binder B

To a sample of yeast-based binder B (667 g) was added Hercosett 617 (67 g, PAE cross-linker; 13% concentration solid cationic polyaminoamide-epichlorohydrin resin), and the resulting composition was mixed at 40° C. until homogeneous. The composition was a free-flowing fluid and its viscosity was measured as being below 500 cP.

Figure 2B:
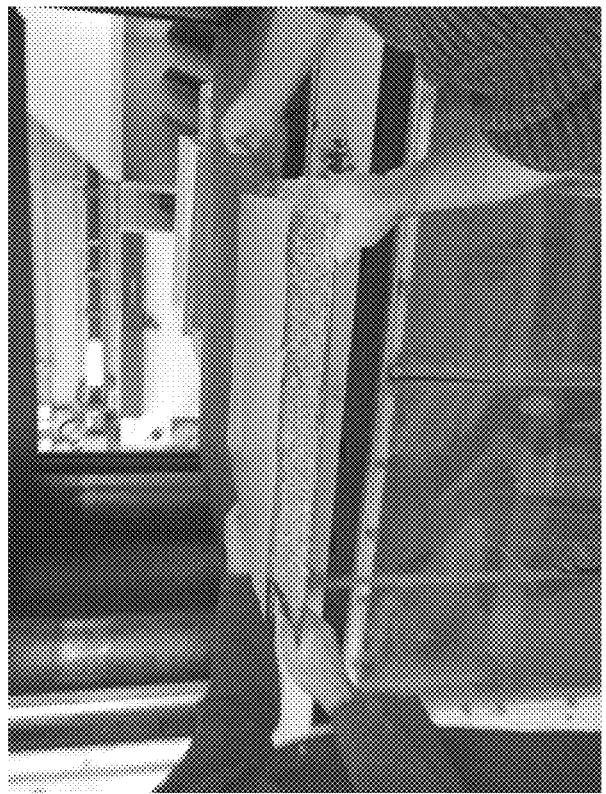
FIG. 2b depicts a mat placed in a heated hydraulic press in accordance with this disclosure.
Figure 2A:
FIG. 2a depicts a resultant mixture that was formed into a mat by hand in accordance with this disclosure.

The binder was spray blended into recycled wood chips or sawdust (10% by weight) with ATRO moisture of 5%, in a 2-meter diameter rotary drum blender, where the binder is pumped into and sprayed from the centre of the drum. The resulting mixture was then formed into a mat by hand, as illustrated by FIG. 2a. The mat is then placed in a heated hydraulic press, as illustrated by FIG. 2b, and pressed at a temperature of 200° C. for 180-300 seconds. The maximal pressure applied was either about 3 MPa or about 4 MPa. The boards produced were either 19.5 mm thick or 14 mm thick. The boards made were either one layered hoards, made from woodchips only, or three-layered boards, including sawdust on the external faces.

Figure 3B:
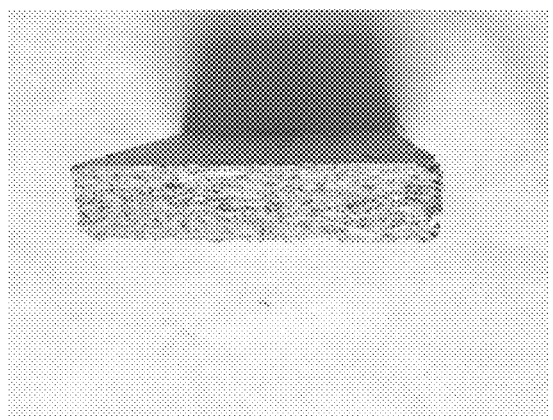
FIGS. 3a-3c depict boards produced by the disclosed process in this disclosure.
Figure 3A:
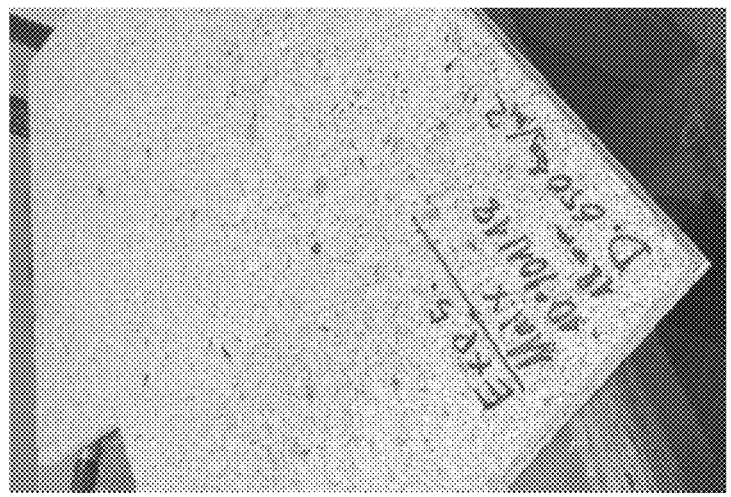
Figure 3D:
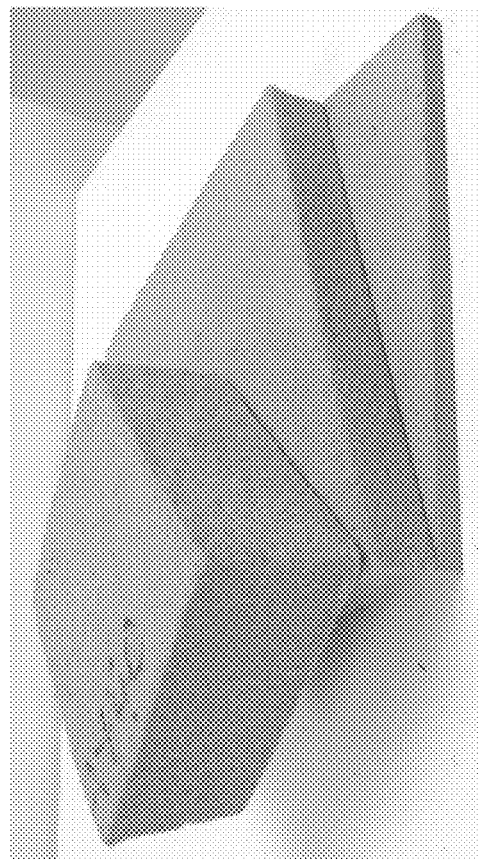
FIG. 3d depicts, from top to bottom, two insulation boards and an MDF board with respective densities of 125, 250 and 750 kg/m$^3$ made using yeast-based binder B with PAE in accordance with this disclosure.
Figure 3C:
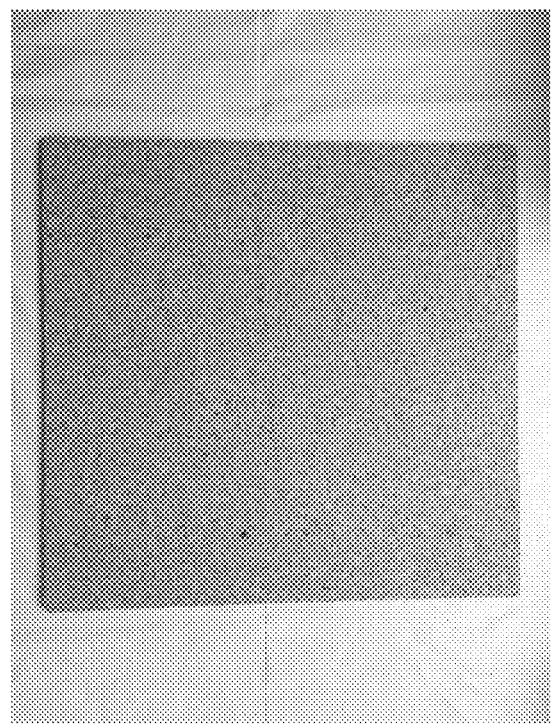

Exemplary boards produced by this process are shown in FIGS. 3a, 3b and 3c.

Insulation boards and MDF boards may also be produced from yeast based binder B with PAE. FIG. 3d illustrates, from top to bottom, two insulation boards and an MDF board with respective densities of 125, 250 and 750 kg/m³ made using yeast based binder B with PAE. 16 one-layered particleboards of size 50 cm² by 50 cm² were produced and tested at specialist centre for composite materials with the purpose of comparing the performance of urea-formaldehyde resin, the invented binder, and a 50% mixture between the latter and melamine- or urea-formaldehyde. Results of these tests are also shown in Table 2 below.

The density of the particleboards is controlled by control of the pressure applied. A larger gap between the plates gives a lower density.

A set of 8 particleboards were made from the binder B+PAE with a lower resin loading.

Tests of these particleboards showed that binder B+PAE has a viscosity that is sufficiently low to be easily mixed to wood. However, the binder B+PAE also maintains a relatively high dry content, allowing for the board to be cured by hot pressing in a relatively short period of time—roughly twice the time taken for the urea-formaldehyde board. This is among the fastest curing times for a bioadhesive (see "Development of sustainable bio-adhesives for engineered wood panels—A Review" RSC Adv., 2017, 7, 38604-38630).

The results also show that binder B+PAE is free of formaldehyde.

Mixing the adhesive with urea- or melamine-formaldehyde was found to reduce formaldehyde emission, whilst maintaining a relatively low resin loading and press closing time.

16 one-layered particleboards (made from recycled woodchips and sawdust) of size 50 cm² by 50 cm² were produced and tested at an industrial facility to compare the performance of the binder of the present invention (8 single-layered boards and one three-layered board tested), and a mixture between the binder of the present invention and melamine- or urea-formaldehyde, and a comparative example of urea-formaldehyde (UF) alone. Results of these tests are shown in Table 2 below.

Particleboards of Size 50 by 50 cm made from Recycled Woodchips and Sawdust at Composite Materials Specialist Center

TABLE 2

| | | | Invented Binder B | | | | |
|---|---|---|---|---|---|---|---|
| | Resin | UF | B + PAE 91%-9% on wet wt. | B + PAE mixture | B + UF 50%-50% on wet wt. | B + MUF mixture | Industry std. (indicative only) |
| Particleboard characterisitcs 19.5 mm thick particleboards can be produced using the invented adhesive | Nbr of layers | 1 | 3 | 1 | 1 | 1 | |
| | Thickness (mm) | 19.7 | 17.0 | 19.5; 14.0 (8 boards) | 19.5 | 19.5 | 19.5 |
| | Density (kg/m^3) | 610 | 710 | 620 | 630 | 620 | 600-750 |
| Mechanical tests Good strength properties | Internal bond strength (N/mm) (BSEN 319) | 0.37 (0.04) | 0.29 (0.03) | 0.22 (0.07) 8x | 0.29 (0.03) | 0.29 (0.05) | >0.24 (P1) |
| | MOR (MPa) (EN310) | 7.3 (1.3) | 7.6 (0.5) | 7.2 (0.4) 1x | 6.7 (0.9) | 6.2 (0.3) | >11.5 (P1) |
| | MOE (MPa) (EN310) | 1360 (240) | 1750 (90) | 1710 (20) 1x | 1280 (130) | 1490 (110) | >1600 (P2) |
| Formaldehyde content The invented adhesive is formaldyhde free | Desiccator (mg/l) (ISO 12480) | | | 0.2 (0.1) 1x | | | <0.30 (F****) |
| | Perforator (mg/100 g) (EN 120) | | | 1.1 (0.1) 1x | | | <1.50 (SE0) |
| Water resistance Suitable for indoor application | Thickness swelling % change after 24 h in water (EN317) | 34% (2) | 41% (2) | 73% (5) 8x | 41% (1) | 26% (1) | P1/P2 not specified |
| | Water absrbtion % chg. after 24 h in water (EN317) | 124% (8) | 109% (3) | 174% (6) 8x | 123% (4) | 103% (5) | |

TABLE 2-continued

| | | | Invented Binder B | | | | |
|---|---|---|---|---|---|---|---|
| Resin | | UF | B + PAE | B + PAE 91%-9% mixture on wet wt. | B + UF | B + MUF 50%-50% mixture on wet wt. | Industry std. (indicative only) |
| Glue mix Low viscosity and good mixing to wood in a roatating drum mixer. | Glue mix board wt. % dry basis (incl. external layer) | 7% | 12% 14% | 7.5% | 6% | 8.5% | UF: 5-10% |
| | Glue mix viscosity (cP) (appoximate) | <400 | <450 | <450 | <450 | <450 | UF: 300-500 |
| Press The invented adhesive cures about 2x slower than UF | Press Temperature (° C.) | 200 | 200 | 180-200 | 180 | 180 | 180-220 |
| | Cooking time (s) | 240 | 300 | 180-340 | 240 | 210 | 110-220 |

Legend
The average values are displayed with standard deviation between brackets.
P1: suitable for general building, joinery
P2: suitable for use in veneering, foiling, kitchen and melaminefacing application
SE0: European perforator method (EN120)
F****: Japanese desiccator method (JIS A 1460)
UF: urea-formaldehyde.
MUF: melamine-formaldehyde.
AN: ammonium nitrate
cP: centipoise, measured usng Zahn cup viscometer The particleboard made from the binder B+PAE with a relatively higher resin loading meets the P1 standard for internal bond strength, and compares favorably to the urea-formaldehyde binder in terms of both MOR and water resistance. Its modulus of elasticity (MOE) is high and meets the P2 standard.

The internal bond strength of all boards with the binder B+UF or MUF was close to or above the P1 industry standard, as measured by BS BSEN 319). The MOR values for each of the boards according to the invention was close to or above the value for the board made from UF alone. The MOE values for each of the boards according to the invention was close to or, in many cases, above the value for the board made from UF alone. The results also show that the invented binder conforms to industry standards on formaldehyde content.

Water resistance of the articles of the present invention after being soaked in water for 24 hours was found to be similar to the ones made from UF.

Resin loading used was 6% to 8.5% of dry resin over oven dried woodchips which is similar to industrial standard for urea-formaldehyde. One particleboard was made with a higher loading of 12%.

Figure 5:
FIG. 5 depicts a 3-layer particleboard in accordance with this disclosure.

FIG. 5 shows a 3-layer particleboard, 19 mm thick, as made according to the invention.

Example 10: Strength Tests

The following binders were prepared:
i) Binder B as described in Example 8
ii) a variant of Binder B using instead of yeast an animal feed yeast containing about 40-60% by weight of a mixture of *Candida* and *Saccharomyces* yeast, and other components such as ashes.
iii) a variant of Binder B using beta-glucan instead of yeast
iv) urea-formaldehyde Strips of size 80 by 25 by 6 mm$^3$ were cut from pine hardwood and each of these adhesives was applied to a surface area of 50×25 mm$^2$ using 150 g/m$^2$ on a dry basis. The two strips were further stacked on top of each other. Some of them were heat pressed during 180 s using a temperature of 180° C. and a pressure of 1.03 MPa. For those hot pressed, PAE described at the beginning of Example 9a was added in the quantities mentioned. They were then stored during 3 days at room temperature. Shear test was performed using a Zwick/Roell universal testing machine pulling at a speed of 2 mm/min. Two samples were produced from each formulation, and the average standard deviation of shear strength test between these two replicates was 0.1 MPa.

Figure 6:
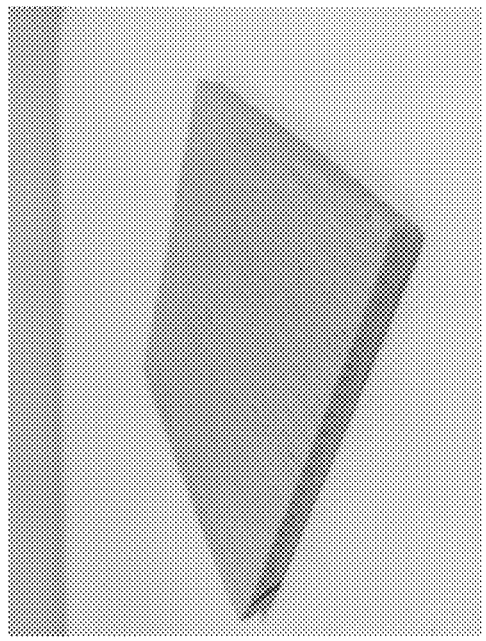
FIG. 6 depicts a 2-ply veneer plywood made from two-layer sheets in accordance with this disclosure.

FIG. 6 shows 2-ply veneer plywood, according to the invention, as made from two-layer sheets.

TABLE 3

| | Average shear test strength (MPa) | |
|---|---|---|
| Adhesive | Self-cured | Hot-pressed |
| Binder B (standard) | 1.0 | 1.7 |
| Using animal feed yeast mixture | 1.2 | |
| β-glucan instead of yeast | | 1.9 |
| Urea-formaldehyde | | 2.2 |

Table 3 above shows that the invented binder is a strong adhesive as compared to conventional adhesives. It illustrates that beta glucans are partly responsible for the adhesion, and that the binder can be made from yeast used as animal feedstock, which may be low-grade yeast.

Example 11: Alternative Yeast-Based Binder—Acid and Alkali Steps Swapped

The procedure described in Example 8 (Synthesis of yeast-based binder B) was followed, except that the addition of HCl and the addition of sodium hydroxide were swapped (i.e. HCl was added before sodium hydroxide). After the HCl was added and mixed in, the pH was measured as about 1. After the sodium hydroxide was added and mixed in, the pH was measured as about 11, which fell to about 9-10 after being left to stand for four hours.

Lab-scale particleboards made using this adhesive, as will be described in Example 12, and hot pressed during 240 seconds had comparable strength to the binder B.

Figure 8:
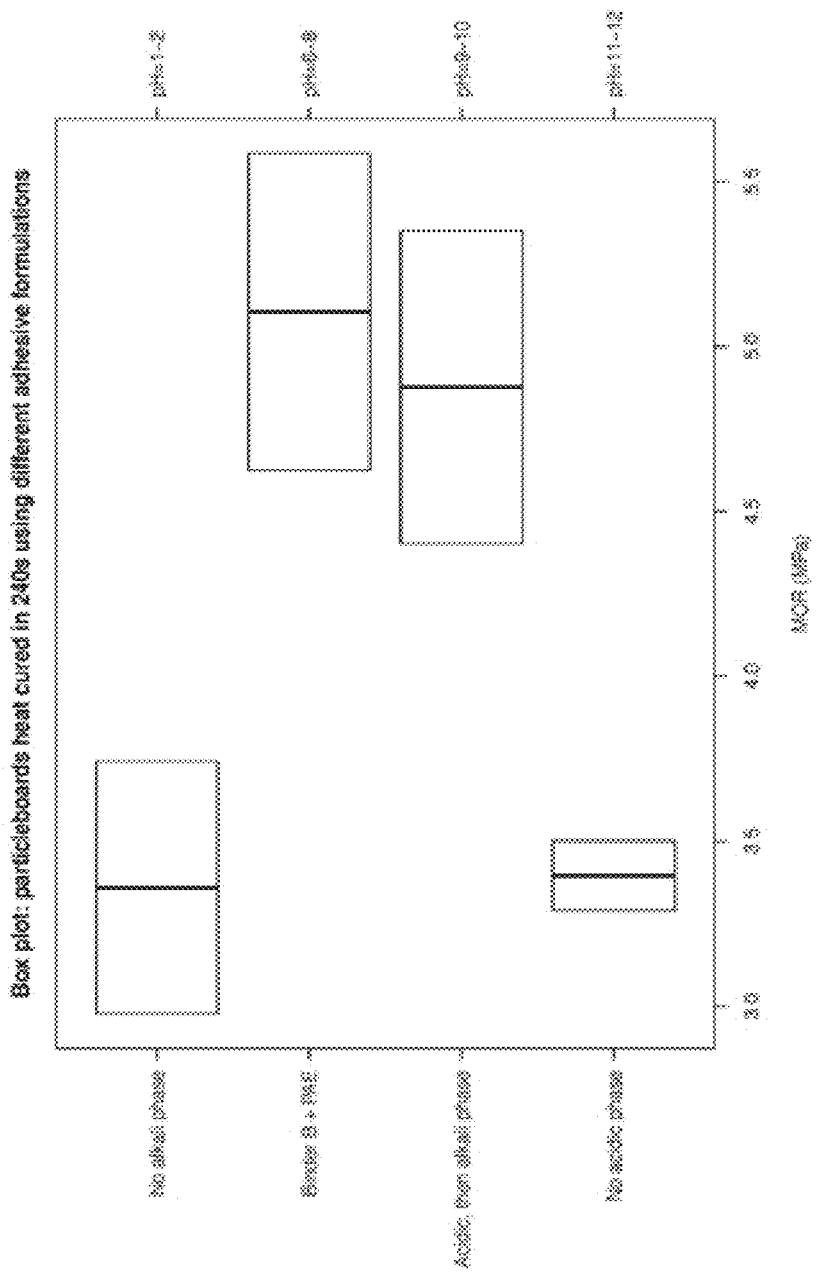
FIG. 8 depicts a boxplot showing results of when acid and alkali are used to produce hinders in accordance with this disclosure.
Figure 9:
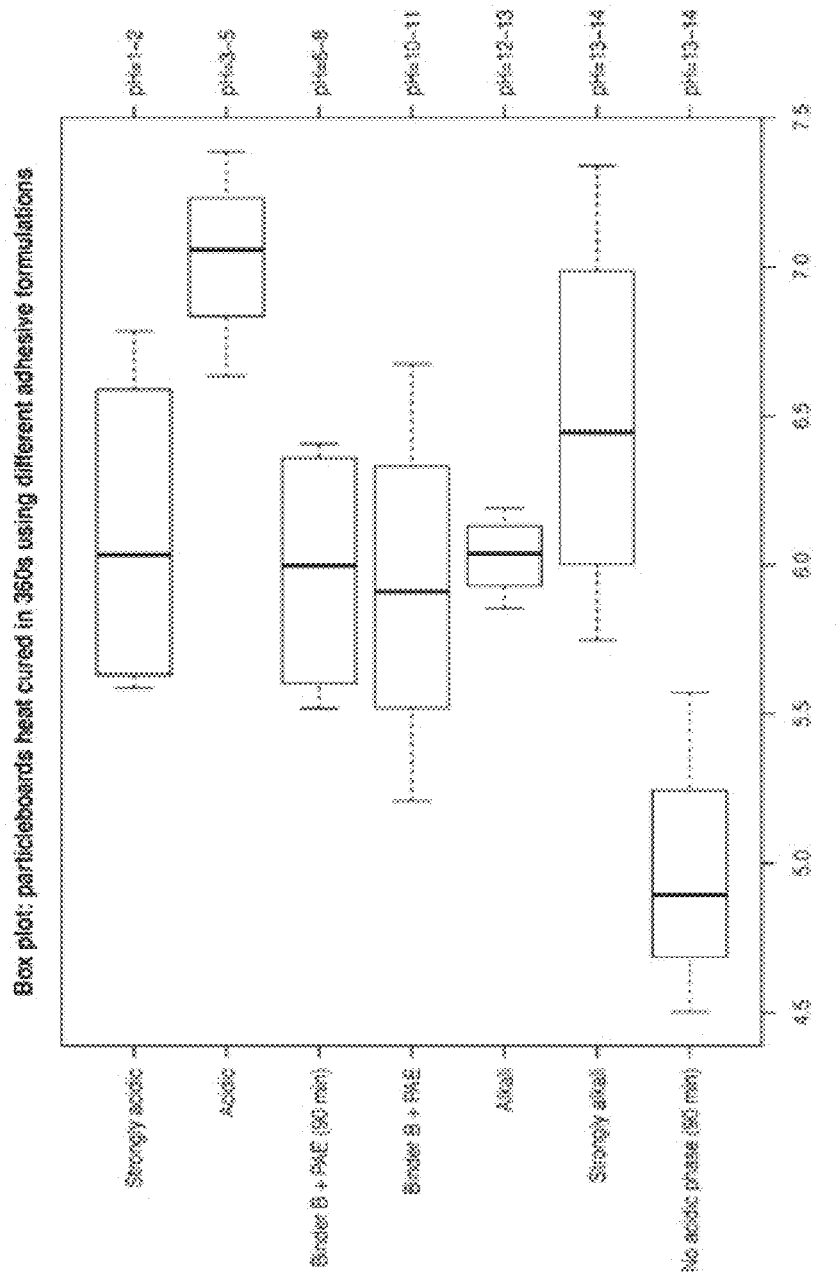

It was determined that when acid and alkali are used to produce hinders, the articles produced from such binders are strong whether the alkali is used before the acid, or whether the acid is used before the alkali. The results are illustrated in the boxplots at FIGS. 7 and 8. There was an average MCA of 5.0 MPa, as shown in the boxplots at FIGS. 7 and 8.

Comparative Example A: Importance of Acid and Alkali

This Comparative Example describes the production of a substance similar to that described in Kadimaliev et al., BioResources (2012) 7(2), 1984-1993.

The procedure described in Example 8 (Synthesis of yeast-based binder B) was followed, except that either the HCl or the sodium hydroxide was not added, and therefore the associated mixing steps were omitted. The omission of HCl afforded a composition with a pH of 12-13, which fell to 11-12 after being left to stand for four hours. The omission of sodium hydroxide afforded a composition with a pH of about 1, which rose to about 2 after being left to stand for four hours.

Lab-scale particleboards were made as described in Example 12. When either the acid or the alkali was omitted, the binder was very difficult to mix with the filler material. The binder stuck to itself more than it stuck to the filler material. FIG. 4a shows an image of a binder according to the present invention on the left. The binder is smooth and glossy and relatively free-flowing. FIG. 4a also shows an example of a binder where the acid had been omitted from the production of the binder, which is matte and significantly more viscous than the binder according to the present invention.

Figure 4B:
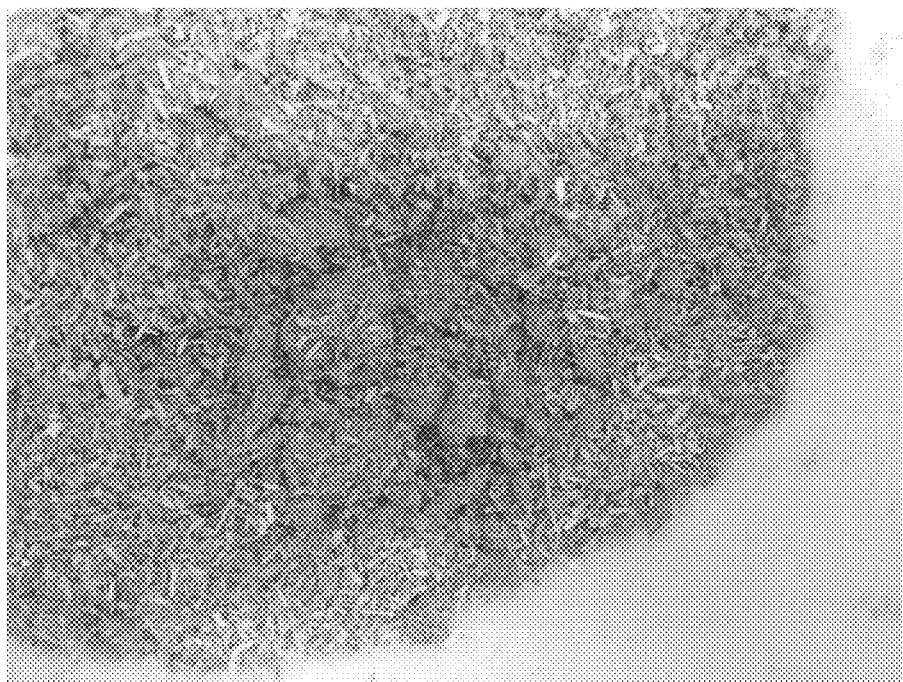
FIG. 4b depicts the mixing of a binder where the acid had been omitted from the production of the binder with sawdust and wood chip in accordance with this disclosure.
Figure 4A:
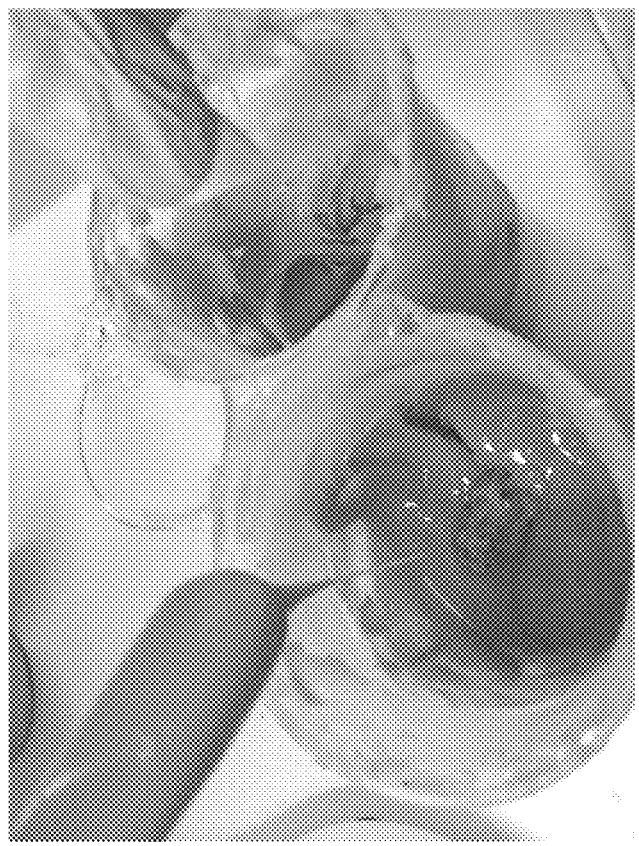
FIG. 4a depicts an image of a hinder in accordance with this disclosure.

FIG. 4b shows the mixing of a binder where the acid had been omitted from the production of the binder with sawdust and wood chip. This binder proved difficult to mix with the filler material because it readily formed clumps and would not coat the filler material.

Particleboards were made using either of these compositions, with a curing time of 240 s, but had a far inferior strength compared to particleboards made using the binder described in Example 8. The boards were easily delaminated by hand, had a low bending strength and were brittle.

Figure 4C:
FIG. 4c depicts a board made from a binder where the acid had been omitted from the production of the binder being broken by hand in accordance with this disclosure.

FIG. 4c shows a board made from a binder where the acid had been omitted from the production of the binder being broken by hand. This board was significantly weaker than similar boards made with binders according to the present invention. The board was able to be broken easily by hand (as shown in FIG. 4c), was significantly more brittle and also delaminated very easily.

Mechanical tests on articles 6 days after they were made from binders where either the acid or the alkali was omitted showed that the MOR had reduced by almost half. A board made from a binder according to the invention had a MOR of 5.1 MPa, whilst a board where either the acid or the alkali was omitted had an average MOR of about 3.4 MPa.

Versions of Binder B defined in Example 8 were produced using the following concentrations of sodium hydroxide, the alkali: 9%, 23%, 37% (standard), 47%, 55%. Two additional versions of Binder B were produced by mixing the alkali phase during 90 minute. The first one was followed by the acidic phase, whereas this phase was omitted for the second one. Two articles (particleboards) were produced using each of these binders by hot pressing during 360 s, and the MOR of each article was determined. The pH of these binders and the MOR of the articles is shown in the boxplots above. It shows that the binder works at any pH, and that the acidic phase cannot be omitted without significantly sacrificing strength of the board. This is also true if the alkali phase is omitted.

Example 12: Comparison of Articles Made from Binder B+PAE with Articles Made from Other Binders Several variations of the binder described in Example 8 were prepared and mixed to 36 g of sawdust and 85 g of woodchips, both having ATRO moisture of about 5%. A mat was then formed and placed in a manual hydraulic 12×12 cm rosin heat press with plate temperature set at 210° C. (the measured temperature was about 170-180° C.). A pressure of 12.4 MPa was maintained for 60 seconds, after which the press handle was kept fixed. Two particleboards were made per formulation (or a single board in the cases denoted by "1xx").

After 5 days at room temperature, they were cut into blocks of about 43×87 mm and their modulus of rupture (MOR) was tested using a universal testing machine with speed strain at 5 mm/s. The MOR was calculated as MOR=(3 F l)/(2 w $t^2$), where F is the maximum load in Newton, l is the support span length, and w and t are the specimen width and thickness respectively, in meters.

Table 4 below details the variations made and the strength of the boards.

To account for the fact that the boards had different densities in practice, a linear regression model was fitted to the data and used to rescale the MOR values so that they correspond to an average density board of 675 kg/m$^3$.

MOR of Lab-Scale Particleboards made from Various Adhesive Formulations

TABLE 4

| Adhesive | Resin loading | Curing time | MOR (MPa) | | t-test |
|---|---|---|---|---|---|
| Invented adhesive | (wt./wood wt., dry) | (s) | mean | sd | p-value |
| Binder B + PAE | 7% | 240 | 5.1 | 0.3 | benchmark |
| 20 min long NaOH phase | | | 5.7 | 0.8 | 0.25 |
| HCl phase before NaOH phase | | | 4.9 | 0.7 | 0.71 |
| Heated at 40° during preparation (1x) | | | 4.3 | 0.1 | — |
| No dextrin | | | 3.8 | 0.3 | 0.00 |
| Using water instead of PAE | | | 3.7 | 0.1 | 0.00 |
| NaOH or HCl phase only | | | 3.4 | 0.3 | 0.00 |
| Binder B + PAE | 7% | 360 | 5.9 | 0.6 | benchmark |
| β-glucan instead of yeast | | | 10.0 | 0.9 | 0.00 |
| 20% yeast substituted by β-glucans | | | 6.8 | 0.7 | 0.11 |
| Animal feed yeast mixture (1x) | | | 6.4 | 0.3 | — |
| 90 min long NaOH phase | | | 6.0 | 0.4 | 0.89 |
| Sulfuric acid instead of HCl | | | 5.5 | 0.8 | 0.33 |
| Ammonium hydrox. instead of NaOH | | | 5.7 | 0.8 | 0.67 |

TABLE 4-continued

| Adhesive | Resin loading | Curing time | MOR (MPa) | | t-test |
|---|---|---|---|---|---|
| Invented adhesive | (wt./wood wt., dry) | (s) | mean | sd | p-value |
| Calcium hydroxide instead of NaOH | | | 5.3 | 0.6 | 0.16 |
| Nitric acid instead of HCl | | | 4.8 | 1.4 | 0.24 |
| 90 min NaOH phase, no HCl phase | | | 5.0 | 0.4 | 0.06 |
| Mushroom powders instead of yeast | 7% | 360 | 4.7 | 0.7 | |
| Made from brewer's yeast residuals | 6% | 480 | 5.7 | 0.2 | |
| Binder B + PAE (1x) | 14% | 480 | 9.5 | 0.7 | |
| Animal feed yeast mixture (1x) | 14% | | 11.8 | 0.3 | |
| Urea-formaldehyde | 11% | 110 | 12.0 | 1.1 | |

Legend
(1x): only two samples from 1 board are tested instead of 2
t-test: unequal variances t-test to test wether the means are equal A range of binders were used in an amount of 7% by weight relative to the weight of the wood and were cured for 240 seconds. Binder B according to Example 8 with PAE had a MOR of 5.1 MPa. Swapping the addition of acid and alkali, such that acid is added before alkali, reduced the MOR of articles made from that composition slightly, to 4.9 MPa. Heating the mixtures at 40° C. reduced the MOR slightly to 4.3 MPa.

When no dextrin (starch) was used, the MOR reduced significantly to 3.8 MPa.

When only either sodium hydroxide or HCl (i.e. just alkali or just acid treatment) was used in the manufacture of the binder, the MOR decreased to an average of 3.4 MPa, which is the lowest value seen in this table.

Therefore, it has been shown that (1) the starch content and (2) the use of both acid and base in the preparation of the binder are key factors in obtaining the desired properties.

When water was used instead of PAE (cross-linker), the MOR was found to be 3.7 MPa. Boards made without the PAE were spongy when they left the press after 240 s, as the core of the board was not well cured.

It is therefore also shown that there is a benefit to including a cross-linker, to obtain the desired properties.

Table 4 also shows that a range of binders were used in an amount of 7% by weight relative to the weight of the wood and were cured for 360 seconds. Under these conditions, the MOR of Binder B with PAE increased to 5.9 MPa. Where 20% of the yeast was substituted by β-glucans, the MOR was found to increase to 6.8 MPa. Using β-glucans instead of yeast significantly increased the MOR of the articles to 10.0 MPa. This rise in strength shows that β-glucans released from within the yeast cells are partly responsible for the adhesive nature of the binder. Increasing the NaOH mixing time to 90 minutes increased the MOR slightly, to 6.0 MPa. However, when the NaOH mixing time was increased to 90 minutes but the acid was omitted, the MOR dropped to 5.0 MPa which is significantly inferior to when both acid and alkali treatments were used. Use of low-grade yeast performed slightly better than standard binder B with PAE, with a MOR of 6.4 MPa. Use of sulfuric acid instead of HCl gave a comparable MOR value of 5.5 MPa. Use of alternative alkalis, instead of NaOH, had only a small effect on the MOR of the article made from that binder, with ammonium hydroxide and calcium hydroxide producing articles with MOR values of 5.7 and 5.3 MPa respectively. The use of nitric acid instead of HCl reduced the MOR value of the articles made from that binder to 4.8 MPa. The use of alternative fungi, instead of yeast, gave a small reduction in the MOR of articles produced from those fungi. Lion's mane, shiitake, chaga and turkey's tail fungi produced articles with MOR values of 4.7 MPa on average.

When the β-glucans were used instead of the yeast, the same acid and alkali steps were used and the same weight amounts were used. The beta glucans were bought from Naturheilpraxisbedarf, a German supplier.

When brewer's yeast residuals were used instead of the normal yeast, a curing time of 480 seconds was used, giving a MOR of 5.7 MPa.

Table 4 also shows that, when a resin loading of 14% by weight and a curing time of 480 seconds is used, the MOR of Binder B with PAE increased to 9.5 MPa. Under these conditions, a similar binder made from low-grade yeast has a MOR of 11.8 MPa. The low-grade yeast contained about 45-50% by weight of a mixture of *Candida* and *Saccharomyces* yeast, as well as other components such as ashes. Low-grade yeast is low in cost and large quantities are available for animal feed.

Conclusion

It has been found that carrying out an alkali treatment and an acid treatment on a starting mixture of fungi or glucan together with starch leads to a binder product that has a paste-like texture. This has low viscosity and can be readily mixed with filler material, such as wood chips or sawdust. This mixture is then shaped and cured to give a 3D shaped article that has excellent strength characteristics. Fast cure times can be achieved, e.g. about 10-18 seconds/mm of thickness.

Without being bound by theory, it is believed that the alkali treatment is lysing the fungi cell walls and solubilizing the basic soluble glucans. During the acid treatment, the acid soluble glucans are getting dissolved, and the glucan is likely getting broken down into smaller polysaccharides.

The starch, e.g. dextrin, is also important—the binding and strength properties are reduced in its absence. Again, without being bound by theory, it is thought the starch interacts with glucans through hydrogen bonding, which strengthens the macromolecular interaction between the binder and the filler material, especially when the filler material comprises wood, as it is thought there is an interaction with cellulose present in the wood that improves the strength of the end product.

A range of fungi starting materials, including animal feed stock yeast, various mushrooms, and baker's yeast, have been shown to work, as have glucans.

The use of a crosslinker is optional but it has been shown that a crosslinker such as a PAE crosslinker gives improved results. Without being bound by theory, it is believed that the crosslinker stabilizes the macromolecular network between the binder and the filler, possibly by reacting with the lignocellulose of the wood and the glucans to stabilize the macromolecular interactions. The crosslink may lead to complex molecular network between the lignocellulose of the wood and the glucans, which is further enhanced by hydrogen bonds and increases the adhesive effect.

Summary of a Preferred Process

1. Provide starting material 1: yeast with a water content of around 1-10 wt %, e.g. 5 wt % in the form of dry powder/pallet. It may be industrial baker's yeast, low grade animal feed yeast, or a by-product of brewer's yeast.
2. Provide starting material 2: Dextrin in the form of dry powder, with a moisture content in the range of 1-10 wt %, e.g. 5 wt %.
3. Mix the dry yeast and dextrin evenly in a mixing vessel, in an amount of 85-99% yeast (e.g. 95%) and 1-15% dextrin (e.g. 5%) by dry weight.
4. Add water to the mixture, to provide an aqueous mixture that has about 45% dry content (e.g. from 35 to 50% dry content).
5. Add a strong alkali solution to the aqueous mixture. The solution preferred is sodium hydroxide with dilution of 35-40% (e.g. about 37%) by weight. Mains water can be the solvent. This helps breaking down the cell wall, especially alkali-soluble glucans. This step is carried out in the mixing vessel for a range of 2-90 minutes, preferentially in the 2-15 minutes range.
6. A strong, dilute acid is then added to the alkalized feedstock. The preferred acid is hydrochloric acid, diluted to a 10-18% (e.g. about 14%) solution by weight. Mains water can be the solvent. This not only helps in bringing the product to neutrality, but also cleaves the bonds of components that have not been broken down during the alkali phase. Some of these include alkali insoluble acid-soluble glucans and mannans, present in the inner cell wall. This step lasts 10-60 minutes, to allow for even blending of the acid solution into the paste. The viscosity of the resulting product is noticeably reduced, allowing for flow outside of the vessel.
7. The resulting paste has a pH in the range of 5 to 8, which over time will normally settle to about 7. It has a rheological behavior similar to a polymer melt, sticking to container walls and flowing steadily.
8. Optional additional water and/or optional additives such as crosslinkers (e.g. PAE resins) and co-binding resins (e.g. isocyanate or formaldehyde based resins) can be added. These also allow the flow regime to change. Crosslinkers and/or co-binding resins are recommended in place of water for this purpose, as water increases the amount of time that the panel product must spend in the press. Small additions can cause large decreases in viscosity. In this example, an addition of 5-10% of PAE (Hercosett 617) by mass of binder can bring the viscosity under 500 cPa, allowing for good fluid flow.
9. The binder is blended with filler materials (e.g. wood chips, wood fibers, sawdust) or applied to various substrates (e.g. veneers or plies), either by hand or using blending machines such as rotating drum mixers and others known in the art. If the binder has a low enough viscosity, then the binder can be sprayed on, for an improved spreading on the substrate.
10. The combined binder and filler materials may be formed into a 3D shape, e.g. a board or panel, whilst the combined binder and substrates may be further stacked or layered to form composite products, such as plywood. The product can be manually compacted in a mould at room temperature, to assume the desired final shape of the product.
11. The pre-pressed shaped article is inserted into a hydraulic heat press for curing under heat and pressure, e.g. for a duration of 180-300 seconds and at a plate temperature of from 150° C. to 250° C. or from 150° C. to 210° C. (e.g. about 200° C.). This cures the binder and forms the final product (e.g., particleboard, oriented strand board (OSB), medium/high density fiberboard (MDF/HDF), insulation boards, plywood). The curing may be carried out under a pressure of from 0.5 to 7 MPa, optionally from 1 to 5 MPa.
12. The final product may be stored to allow cooling and the completion of the curing process (e.g. for 3 days-2 weeks)

The subject matter of the following clauses is also provided:

1. A method for producing a shaped article, the method comprising:
    a) providing a fungi-based binder having a pH from 5 to 9, wherein the fungi-based binder has been produced by
        i. mixing fungi with an alkaline agent to form an alkaline composition; and
        ii. mixing the alkaline composition with an acidic agent to form the fungi-based binder having a pH from 5 to 0;
    b) forming a binder composition by mixing the binder, optionally with filler material;
    c) shaping the binder composition into a three-dimensional shape; and
    d) curing the composition to form a shaped article having said three-dimensional shape.

The binder may include starches, such as dextrin and other modified starches. The composition may be cured at elevated temperature and/or pressure. The composition may be shaped into a three-dimensional shape, which is the desired shape of the shaped article, before or during curing.

2. The meghod of clause 1, wherein step a) comprises producing the fungi-based binder, by carrying out the steps of:
    i. mixing fungi with an alkaline agent to form an alkaline composition; and
    ii. mixing the alkaline composition with an acidic agent to form the fungi-based binder,
wherein the quantities of alkaline agent and acidic agent are selected such that the resulting fungi-based binder has a pH from 5 to 9.

3. The method of clause 1 or clause 2, wherein the fungi-based binder has a pH of:
    a) from 5.5 to 8; or
    b) from 6 to 8.

4. The method of any one of the preceding clauses, wherein the alkaline agent is provided as an aqueous solution with an alkali concentration of:
    (a) from 2% to 50% by weight,
    (b) from 10% to 50% by weight, or
    (c) from 15% to 45% by weight.

5. The method of any of the preceding clauses, wherein the alkali used in the alkaline agent has a pKaH of:
   (a) 9 or greater,
   (b) 10 or greater, or
   (c) 11 or greater.

6. The method of any one of the preceding clauses, wherein the acidic agent is provided as an aqueous solution with a concentration of acid of:
   (a) from 2% to 50% by weight,
   (b) from 10% to 50% by weight, or
   (c) from 15% to 45% by weight.

7. The method of any one of the preceding clauses, wherein the acid in the acidic agent has a pKa of:
   (a) 5 or less, or
   (b) 4 or less,
   (c) 3 or less.

8. The method of any one of the preceding clauses, wherein the binder makes up
   (a) from 5 to 90%,
   (b) from 10% to 75%,
   (c) from 15 to 60%, or
   (c) from 20 to 50%
by weight of the composition formed in step b).

9. The method of any one of the preceding clauses, wherein in step b( the binder composition is formed by mixing the binder with filler material.

10. The method of clause 9, wherein the filler material comprises one or more materials selected from: wood-based filler, fly ash, mineral solid residue such as egg shells, algae, feathers, hemp, bonemeal, plastics, granulate fertilizer, flour, flax fiber and combinations thereof.

11. the method of clause 9 or clause 10, wherein the filler material comprises:
   (a) microalgae; and/or
   (b) wood-based filler; and/or
   (c) feathers; and/or
   (d) flour.

12. The method of any one of clauses 9 to 11, wherein the filler material makes up
   (a) from 10% to 90%,
   (b) from 15 to 85%,
   (c) from 40 to 85%,
   (d) from 50 to 80%,
by weight of the composition formed in step b).

13. The method of any one of the preceding clauses, wherein one or more additive is included in the composition formed in step b).

14. The method of any one of the preceing clauses, wherein the composition is placed in a mould in step c), such that the article takes on the shape of the mould when it cures in step d).

15. The method of any one of clauses 1 to 13, wherein the composition is 3D printed in step c) or pressed into a 3D shape in step c).

16. An article obtainable by the method of any one of clauses 1 to 15.

17. The article of clause 15, which is a packaging article, a construction article, or a furniture article.

18. The article of clause 17, which is a flooring tile.

19. A flooring structure comprising a plurality of the articles as defined in clause 18 temporarily or permanently linked together in a planar array.

20. A method for preparing a binder, compsiring the step of mixing fungi with an alkaline agent to form an alkaline composition, and mixing the alkaline composition with an acidic agent, wherein the alkaline agent is provided as an aqueous solution of an alkali which has a pKaH of 11 or more and with the alkali concentration being 10% or more by weight of the alkaline agent, and
wherein the acidic agent is provided as an aqueous solution of an acid which has a pKa of 2 or less and with the acid concentration being 10% or more by weight of the acidic agent.

21. The invention of any one of the preceding clauses, wherein the fungi is:
   (a) in the phylum Ascomycota; or
   (b) a yeast; or
   (c) a yeast of the *Saccharomyces* species.

22. The invention of clause 20, wherein the yeast is a *Saccharomyces cerevisiae* yeast.

23. The invention of any one of the preceding clauses, wherein the alkaline agent is an aqueous solution of sodium hydroxide, potassium hydroxide, rubidium hydroxide, caesium hydroxide, calcium hydroxide or strontium hydroxide.

24. The invention of any one of the preceding clauses, wherein the ratio of alkaline agent to fungi, by weight, is
   (a) from 4:1 to 1:4,
   (b) from 3:1 to 1:3,
   (c) from 2:1 to 1:2, or
   (d) from 1.5:1 to 1:1.5.

25. The invention of any one of the preceding clauses, wherein the acidic agent is selected from an aqueous solution of hydrochloric acid, hydrofluoric acid, sulfuric acid, nitric acid, phosphoric acid, carbonic acid, citric acid, lactic acid and acetic acid.

26. The invention of any one of the preceding clauses, wherein the ratio of acid agent to fungi, by weight, is:
   (a) from 4:1 to 1:4,
   (b) from 3:1 to 1:3,
   (c) from 2:1 to 1:2, or
   (d) from 1.5:1 to 1:1.5.

27. The invention of any one of the preceding clauses, wherein the molar ration of acid to alkali is
   (a) from 1:15 to 1.5:1,
   (b) from 1:1.3 to 1.3:1, or
   (c) from 1:1.1 to 1.1:1.

28. The invention of any one of the preceding clauses, wherein the fungi-based binder has a pH of 7.

29. A binder obtainable by the method of clause 20 or any one of clauses 21 to 28 as dependent on clause 20.

30. A method of adhering two component parts to produce a composite product, each component part having a contact surface, the method comprising:
   a) providing a fungi-based binder as defined in clause 29;
   b) applying the binder to the contact surface of the first component part and/or the contact surface of the second component part;
   c) contacting the contact surface of the first component part with the contact surface of the second component part; and
   d) curing the binder to provide the composite product.

31. The method of clause 30, wherein step a) comprises producing the binder by carrying out the method of clause 20 or any one of clauses 21 to 28 as dependent on clause 20.

32. A composite product obtainable by the method of clause 30 or clause 31.

What is claimed is:

1. A method for producing a shaped article, the method comprising:
   a) providing a binder, wherein the binder has been produced by a process of:
      i) mixing (A) fungi or glucan and (B) starch with an alkaline agent to form an alkaline composition; and mixing the alkaline composition with an acidic agent to form the binder; or
      ii) mixing (A) fungi or glucan and (B) starch with an acidic agent to form an acidic composition; and mixing the acidic composition with an alkaline agent to form the binder;
   b) forming a binder composition by mixing the binder with filler material;
   c) shaping the binder composition into a three-dimensional shape; and
   d) curing the binder composition to form a shaped article having said three-dimensional shape;
   wherein step c) and step d) can be carried out simultaneously or separately,
   and wherein during one or both of step c) and step d) pressure is applied to the binder composition.

2. The method of claim 1, wherein the filler material comprises wood and the shaped article is an engineered wood product.

3. The method of claim 1, wherein in the composition as formed in step
   b) the binder makes up:
   (a) from 2 to 90%,
   (b) from 2% to 50%, or
   (c) from 5 to 25% by weight of the composition, when considered on a wet weight basis.

4. The method of claim 1, wherein in the composition as formed in step
   b) the filler material makes up:
   (a) from 10% to 99%,
   (b) from 15 to 95%,
   (c) from 40 to 95%,
   (d) from 70 to 95%, or
   (e) from 70 to 90%,
   by weight of the composition, when considered on a wet weight basis.

5. A method for producing a shaped article which is an engineered wood product, the method comprising:
   a) providing a binder, wherein the binder has been produced by a process of:
      i) mixing (A) fungi or glucan and (B) starch with an alkaline agent to form an alkaline composition; and mixing the alkaline composition with an acidic agent to form the binder; or
      ii) mixing (A) fungi or glucan and (B) starch with an acidic agent to form an acidic composition; and mixing the acidic composition with an alkaline agent to form the binder;
   b) forming a three-dimensional shape by combining the binder and a plurality of component parts, with there being three or more component parts in the form of layers, each comprising wood, and with layers of binder being provided between the layers of wood; and
   c) curing the three-dimensional shape under pressure to form a shaped article having said three-dimensional shape.

6. The method of claim 1, wherein step a) comprises producing the binder in situ, by carrying out process i) or process ii).

7. The method of claim 1, wherein the curing is carried out a temperature from 15° C. to 250° C.

8. The method of claim 1, wherein the curing is carried out under a pressure from 0.5 to 7 MPa, optionally from 1 to 5 MPa.

9. A method for preparing a binder, comprising the steps of:
   i) mixing (A) fungi or glucan and (B) starch with an alkaline agent to form an alkaline composition; and mixing the alkaline composition with an acidic agent to form the binder; or
   ii) mixing (A) fungi or glucan and (B) starch with an acidic agent to form an acidic composition; and mixing the acidic composition with an alkaline agent to form the binder.

10. The method of claim 1, wherein the starch comprises dextrin.

11. The method of claim 1, wherein the binder as made by step a) i) or ii) and as measured after being allowed to stand for four hours has a pH of:
   i) from 3 to 10; or
   ii) from 4 to 9; or
   iii) from 5 to 9; or
   iv) from 5.5 to 8; or
   v) from 6 to 8.

12. The method of claim 1, wherein the ratio of dry starch to dry fungi/glucan by weight, is
   (a) from 1:200 to 1:2.5; or
   (b) from 1:200 to 1:5; or
   (c) from 1:200 to 1:10.

13. The method of claim 1, wherein the starting material comprising (A) fungi or glucan and (B) starch is provided as an aqueous mixture with a dry content (i.e. the components that are not water), by weight, of:
   (a) from 10% to 55%;
   (b) from 20% to 55%; or
   (c) from 35% to 50%.

14. The method of claim 1, wherein the alkaline agent is added in the form of an aqueous solution that has an alkali concentration of:
   (a) from 2% to 60% by weight,
   (b) from 10% to 50% by weight, or
   (c) from 15% to 45% by weight.

15. The method of claim 1, wherein the alkali used in the alkaline agent has a pKaH of:
   (a) 9 or greater,
   (b) 10 or greater, or
   (c) 11 or greater.

16. The method of claim 1, wherein the acidic agent added in the form of an aqueous solution that has a concentration of acid of:
   (a) from 2% to 50% by weight,
   (b) from 10% to 50% by weight, or
   (c) from 15% to 45% by weight.

17. The method of claim 1, wherein the acid in the acidic agent has a pKa of:
   (a) 5 or less, or
   (b) 4 or less,
   (c) 3 or less.

18. The method of claim 1, wherein the fungi are:
   (a) a Dikarya;
   (b) in the phylum Ascomycota or the family basidiomycota; or
   (c) a yeast; or
   (d) a yeast of the *Candida* or *Saccharomyces* genera; or
   (e) a yeast of the *Saccharomyces* genus.

19. The method of claim 18, wherein the yeast is a *Saccharomyces cerevisiae* yeast.

20. The method of claim 1, wherein the alkaline agent is an aqueous solution of sodium hydroxide, potassium hydroxide, rubidium hydroxide, caesium hydroxide, calcium hydroxide or strontium hydroxide.

21. The method of claim 1, wherein the ratio of alkaline agent to dry fungi/glucan, by weight, is
   (a) from 5:1 to 1:15,
   (b) from 3:1 to 1:15, or
   (c) from 2:1 to 1:10.

22. The method of claim 1, wherein the acidic agent is selected from an aqueous solution of hydrochloric acid, sulfuric acid, nitric acid, phosphoric acid, carbonic acid, citric acid, lactic acid, formic acid and acetic acid.

23. The method of claim 1, wherein the ratio of acidic agent to dry fungi/glucan, by weight, is:
   (a) from 5:1 to 1:15,
   (b) from 3:1 to 1:15,
   (c) from 2:1 to 1:10, or
   (d) from 1:1 to 1:10.

24. The method of claim 1, wherein the molar ratio of acid to alkali is
   (a) from 5:1 to 1:30,
   (b) from 2:1 to 1:10, or
   (c) from 1:1 to 1:6.

25. The method of claim 1, wherein the binder further comprises a curing agent.

26. The method of claim 25, wherein the crosslinker selected from: polyamidoamine epichlorohydrin (PAE) resin and epoxy resins.

27. The method of claim 25, wherein the crosslinker is included in an amount of from 0.1% to 30% by weight, optionally from 1% to 30% by weight.

28. The method of claim 1, wherein the binder is used in combination with a co-resin, with the co-resin being used in an amount of up to 60% by weight of the combined binder plus co-resin.

29. The method of claim 28, wherein the co-resin is selected from the group consisting of urea-formaldehyde, melamine-formaldehyde, and pMDI.

30. A method of adhering two component parts to produce a composite product, each component part having a contact surface, the method comprising:
   a) carrying out the method of claim 9 to provide a binder;
   b) applying the binder to the contact surface of the first component part and/or the contact surface of the second component part;
   c) contacting the contact surf ace of the first component part with the contact surf ace of the second component part; and
   d) curing the binder to provide the composite product.

* * * * *